(12) United States Patent
Krahbichler

(10) Patent No.: US 9,579,182 B2
(45) Date of Patent: Feb. 28, 2017

(54) METHOD FOR DELIVERY OF AN EMBOLIC PROTECTION UNIT

(71) Applicant: SWAT Medical AB, Helsingborg (SE)

(72) Inventor: Erik Krahbichler, Helsingborg (SE)

(73) Assignee: SWAT Medical AB, Helsingborg (SE)

( * ) Notice: Subject to any disclaimer, the term of this patent is extended or adjusted under 35 U.S.C. 154(b) by 598 days.

(21) Appl. No.: 14/080,703

(22) Filed: Nov. 14, 2013

(65) Prior Publication Data

US 2014/0180329 A1    Jun. 26, 2014

Related U.S. Application Data

(60) Provisional application No. 61/726,540, filed on Nov. 14, 2012.

(51) Int. Cl.
*A61M 29/00* (2006.01)
*A61F 2/01* (2006.01)
*A61F 2/24* (2006.01)
*A61M 25/00* (2006.01)

(52) U.S. Cl.
CPC .............. *A61F 2/013* (2013.01); *A61F 2/24* (2013.01); *A61F 2230/0093* (2013.01); *A61M 2025/0063* (2013.01)

(58) Field of Classification Search
CPC .............. A61F 2/013; A61F 2002/011; A61F 2250/0059; A61F 2/2427; A61F 2/243; A61F 2/2433; A61F 2230/0093; A61M 2025/1047; A61M 25/1011
USPC ......................................... 606/200; 623/2.11
See application file for complete search history.

(56) References Cited

U.S. PATENT DOCUMENTS

| | | | |
|---|---|---|---|
| 6,395,014 B1 * | 5/2002 | Macoviak | A61F 2/013 606/194 |
| 2012/0172915 A1 * | 7/2012 | Fifer | A61F 2/013 606/200 |
| 2013/0238010 A1 * | 9/2013 | Johnson | A61F 2/013 606/200 |
| 2013/0245669 A1 * | 9/2013 | Basu | A61F 2/013 606/200 |

* cited by examiner

*Primary Examiner* — Katherine M Shi
(74) *Attorney, Agent, or Firm* — Inskeep IP Group, Inc.

(57) ABSTRACT

A method of delivering a embolic protection unit to the aorta arch of a patient. The method comprising, introducing a catheter from brachiocephalic artery or through an incision in a wall of the ascending aorta, the catheter comprising an embolic protection unit having an off-center connection point. Advancing the embolic protection unit in a downstream direction from the catheter. Expanding the embolic protection unit in the aorta arch to cover said ostia. Delivering a medical device into the ascending aorta while the embolic protection unit is hold by the catheter covering the ostia.

18 Claims, 17 Drawing Sheets

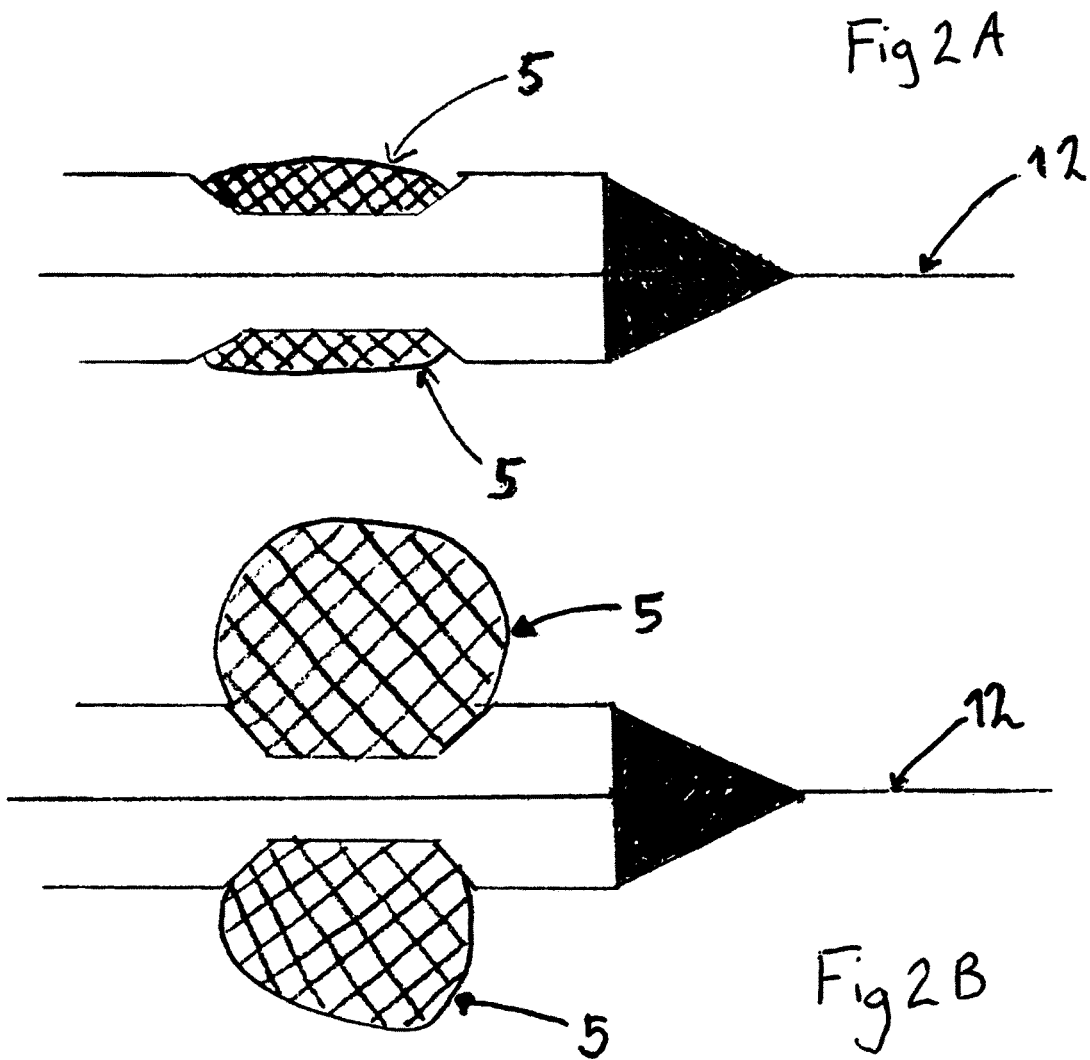

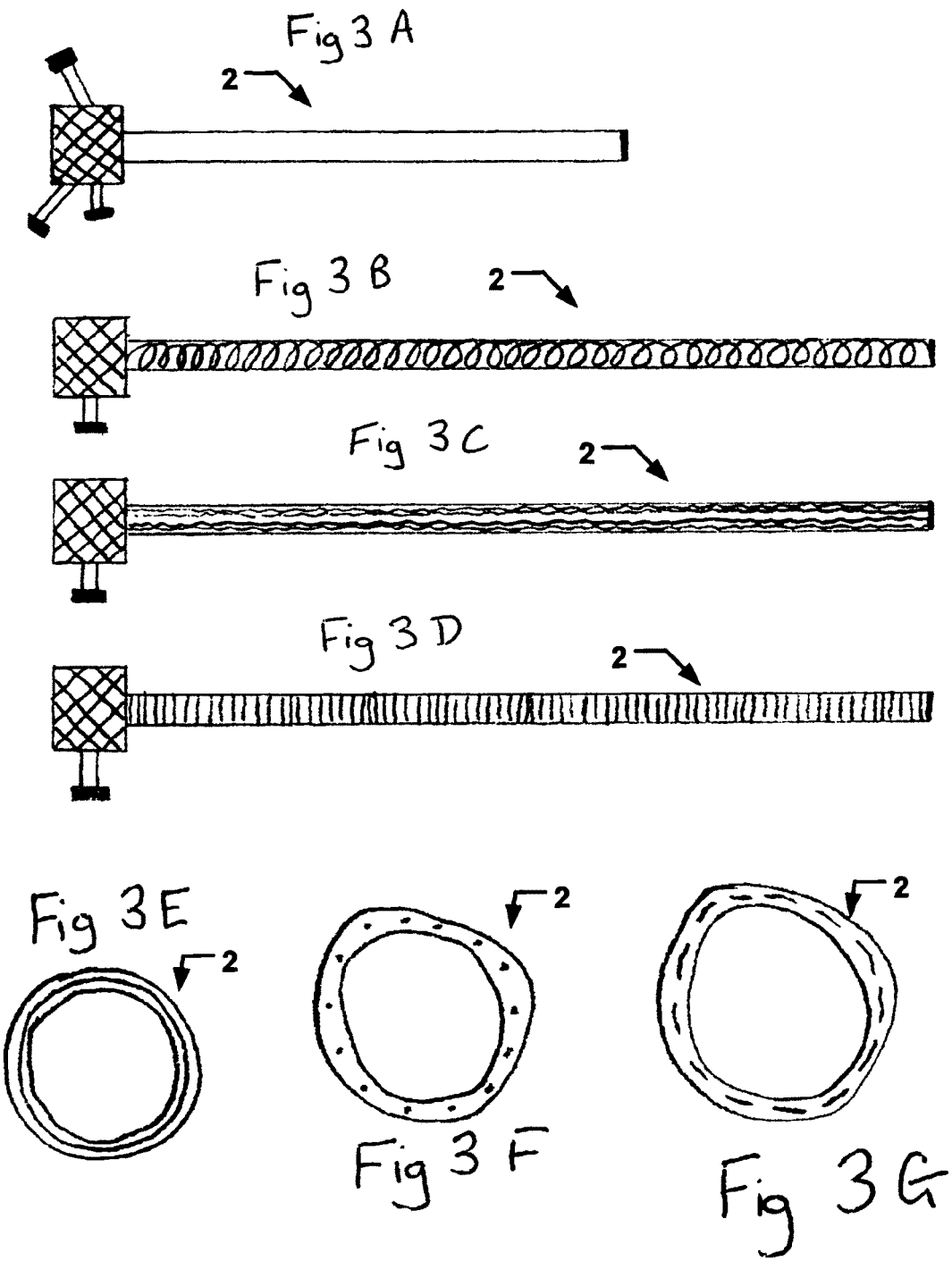

METHOD FOR DELIVERY OF AN EMBOLIC PROTECTION UNIT

RELATED APPLICATIONS

This application claims priority to U.S. Provisional Application Ser. No. 61/726,540 filed Nov. 14, 2012 entitled Method For Delivery Of An Embolic Protection Unit, which is hereby incorporated herein by reference in its entirety.

FIELD OF THE INVENTION

This invention pertains in general to the field of medical devices. In particular the invention relates to the positioning of catheters for the delivery of an embolic protection unit together with a medical devices or a medical procedure, and more specifically to the delivery of an embolic protection unit to the aorta arch.

BACKGROUND OF THE INVENTION

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Endovascular procedures are being used more and more frequently to treat various cardiac and vascular surgical problems. Blocked arteries can be treated with angioplasty, endarterectomy, and/or stenting, using minimally invasive endovascular approaches. Aneurysms can be repaired by endovascular techniques. Another use for endovascular surgery is the treatment of cardiac valvular disease. Valvuloplasties are done endovascularly and percutaneous valve replacement is becoming an established procedure. Transcatheter Aortic Heart Valve (TAVI) is a procedure involving a collapsible aortic heart valve that can be manipulated into place with minimally-invasive techniques.

Cerebral embolism is a known complication of such endovascular procedures, and other cardiac surgery, cardiopulmonary bypass and catheter-based interventional cardiology, electrophysiology procedures etc. Embolic particles may include thrombus, atheroma and lipids, plaque found in the diseased vessels and valves that is dislodged and results in embolization. Embolic particles may become dislodged by surgical or catheter manipulations and enter the bloodstream. Dislodged embolic particles can thus embolize into the brain downstream. Cerebral embolism can lead to neuropsychological deficits, stroke and even death.

Prevention of cerebral embolism benefits patients and improves the outcome of these procedures. Embolic protection devices should be compatible with the endovascular procedures, and for instance not hinder passage through the aortic arch to the heart.

Various embolic protection devices are known in the art.

Some embolic protection devices are disclosed in WO 2012/009558 A2, or WO 2012/085916 A2, which are incorporated herein in their entirety for all purposes. However, these devices may provide iatrogenic damage to the vessels in which they are positioned. The devices also have a rather high profile in the aortic arch, limiting the endovascular procedures.

More advantageous low profile planar devices for embolic protection of side branch vessels of the aortic arch have for instance been disclosed in WO 2010/026240 A1 or are described in international patent application number PCT/EP2012/058384, which are incorporated herein in their entirety for all purposes.

The devices may however be further improved. One issue is that blood, that may include embolic particles, may impair efficiency of the devices by bypassing across the device at the periphery thereof to the carotid arteries due to insufficient sealing at the periphery.

"Sailing" of the devices in the high pressure bloodstream ejected out of the heart is another issue.

Hence, notwithstanding the efforts in the prior art, there remains a need for a further improved embolic protection devices of the type that can permit endovascular procedures, in particular of the heart, while protecting the cerebral vasculature during the procedures.

Further, in some instances a direct aorta approach TAVI procedure may still be a preferred option, for example patients with any aortic root angle be treated. Direct aortic access may be indicated for patients with vessel diameters <6 mm, heavy peripheral calcification, excessive tortuosity or subclavian stenosis. The most appropriate access route should be selected by the cardiovascular team based on patient anatomical and clinical characteristics. Hence a protection device and a delivery device that can be used for more than one access may be advantageous.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device or method according to the appended patent claims for providing temporary embolic protection to a patient's aortic arch vessels during medical procedures, such as cardiac surgery and interventional cardiology and electrophysiology procedures. Embolic particles in the aortic blood flow are prevented from entering the aortic arch side branch vessels, including the carotid arteries that lead to the brain.

Disclosed herein are systems and methods for delivery of embolic deflection.

According to one aspect of the disclosure, a method of delivering an embolic protection unit to the aorta arch of a patient is disclosed. The method comprises introducing a catheter from brachiocephalic artery or through an incision in a wall of the ascending aorta. The catheter comprises an embolic protection unit having an off-center connection point. The method further comprising advancing the embolic protection unit in a downstream direction from the catheter, expanding the embolic protection unit in the aorta arch to cover the ostia, and delivering a medical device into the ascending aorta while the embolic protection unit is hold by the catheter covering the ostia.

Some examples of the method includes, the embolic protection unit is expanded to a non-tubular, substantially planar shape over the ostia.

Some examples of the method includes, the catheter is introduced towards the cardiac valves coaxially the ascending aorta, or wherein the medical device is introduced towards the cardiac valves coaxially the ascending aorta.

Some examples of the method includes, the catheter comprises at least two channels, an elongated sheath with a first channel and a second channel from which the embolic protection unit is expanded, the second channel is arranged in the first channel or around the sheath.

Some further examples of the method includes, introducing a pigtail through one of the channels. A pigtail catheter may be provided in such an auxiliary side channel. The pigtail catheter may be used to further stabilize the catheter against the annulus of the aortic valve and inner wall of the aortic arch, such as described in WO 2012/094195 A1, which is incorporated herein by reference in its entirety for all purposes, see in particular. A pigtail may also be used to determine were to make the incision when performing a direct aorta approach.

Some further examples of the method includes, the second channel is arranged helically around the elongated sheath, and wherein the second channel has an opening directed at an angle away from an opening of the first channel, such as in a direction toward aorta arch when the opening of the first channel is directed towards the ascending aorta.

This arrangement may facilitate introducing and directing of the collapsed embolic protection unit since the opening of the second channel is directed towards the aorta arch and not parallel with the first channel which may be directed coaxial with the ascending aorta, for example when performing the direct aorta approach.

Some further examples of the method includes, radially expanding expandable units of the catheter or an elongated member positioned beyond a distal end of the elongated sheath, to temporarily position in relation to the valve the elongated sheath. The method further includes releasing locking members of the catheter to maintain the elongated sheath in a locked state, delivering a medical device through the first channel to the cardiac valve, releasing the locking members to return the elongated sheath to a relaxed state, and withdrawing the elongated sheath in the relaxed state from the vasculature of the patient.

Some further examples of the method includes, inserting an elongated member with a distal end portion comprising a plurality of the radially expandable units, into a lumen of the elongate sheath. Advancing the elongated member through the elongated sheath to the distal end of the elongated sheath and retracting the expandable units and withdrawing the elongated member from the lumen of the elongated sheath.

Some further examples of the method includes, making an incision in a wall of the ascending aorta upstream the introduced catheter for introducing the medical device while the embolic protection unit is protecting the ostia.

Some further examples of the method includes, introducing the catheter in a direction towards the aorta arch and retracting the catheter after expanding the embolic protection unit in the aorta arch. Also, forwarding the catheter towards the cardiac valves coaxially the ascending aorta and using at least one tissue apposition sustaining unit, not being a delivery shaft of the embolic protection unit, for application of a force offset to the connection point at the embolic protection unit, such as a periphery, towards an inner wall of the aortic arch when the embolic protection unit is positioned in the aortic arch, such that tissue apposition of the periphery to an inner wall of the aortic arch is supported by the force.

This method is less iatrogenic than known methods. It provides for further improved sealing of the periphery of an embolic protection device. It further prevents creation of debris from an ostium in the aortic arch, which might be an issue with some known embolic protection devices.

The supported apposition is improving apposition of the periphery to the inner wall of the aortic arch, such that the improved apposition provides for improved sealing of the periphery against the inner wall.

The force may be applied in a substantially proximal direction relative the device for the improved sealing.

Applying the force may include applying a tractive force by a traction unit. The tractive force may include pulling a periphery of the device against the inner wall for locking the device in place in the aortic arch. The tractive force may be applied by at least one tether distally connected to the frame, periphery and/or blood permeable unit for providing the tractive force.

The device may be delivered to the aortic arch via one of the side vessels, such as the brachiocephalic artery from the right subclavian artery, the left carotid artery, or the left subclavian artery. It may be delivered to the aortic arch via the descending aorta such as in a femoral approach, e.g. in a side channel of a main catheter. It may be delivered to the aortic arch through the wall of the ascending aorta, which is an approach called "direct aorta" approach.

Applying the force includes applying a tractive force by a traction unit, such a tether, or a pushing force by a pushing unit.

Some further examples of the method include a medical device which is a bypass machine. Also, the medical device is for a TAVI procedure where a stent valve is delivered while the embolic protection unit is positioned and with the catheter in the aorta arch. Alternatively the medical device is a device for electrophysiology.

Some further examples of the method includes, advancing the embolic protection unit in a downstream direction from the catheter which comprising, advancing a second catheter through a channel of the catheter, the second catheter has a retractable sheath enclosing the embolic protection unit and retracting the sheath whereby the embolic protection unit expands.

The second catheter has a distal end having a bend. This may facilitate the directing of the second catheter if the opening of the second catheter is directed coaxial with the ascending aorta.

Also the method may include, introducing the catheter which includes placing a balloon mounted on the catheter with expanding the balloon in the ascending aorta.

The balloon is a donut shaped balloon having a filter between the catheter and the inner ring of the donut shape.

The term "sustain" as used herein means one of support, aid, assist, keep up, uphold or the like. Sustaining a tissue apposition of a device according to the present disclosure may be provided by a push force or a pull force supporting, aiding or assisting apposition, depending on the specific examples.

The term "tether" as used herein shall not be confused with a safety tether, which is a simple safety line for allowing retrieval of an embolic protection device if needed. A tether as used herein is a line allowing controlled tensioning of an entire embolic protection device or selected portions thereof. Traction is applied proximally to the tether for the providing the tensioning of the device to an inner vessel. The tether is distally connected or attached to the embolic protection device such that the traction supports anchoring of the device against the inner vessel wall. In this manner a fluid flow at the periphery of the device is controllable and can be totally stopped by the degree of traction on the tether such that blood only passes a blood permeable unit of the device.

The device including the inventive improvement of examples, includes a collapsible embolic protection device devised for temporary transvascular delivery to an aortic arch of a patient, the device having a protection unit including a selectively permeable material or unit adapted to prevent embolic material from passage with a blood flow into a plurality of aortic side branch vessels at the aortic arch, wherein the protection unit is permanently or releasably (for assembly prior to introduction into the body) attached to a transvascular delivery unit at a connection point or region, or an attachment point, provided at the selectively permeable unit, and a first support member for the protection unit that is at least partly arranged at a periphery of the selectively permeable unit. In an expanded state of the device, the connection point is enclosed by the first support member or integral therewith, wherein the transvascular delivery unit is connected off-center to the protection unit at the connection point. In some examples, the connection point or region, or attachment point, is enclosed by the first support member.

The connection point may be provided at the selectively permeable unit or at the first support member.

The connection point may be provided on a surface of the selectively permeable unit devised to be oriented towards the aortic side branch vessels from inside the aortic arch and at a distance from the ostia regions when the protection unit is positioned in the aortic arch.

In some examples, the selectively permeable unit includes a first portion devised to extend in a first direction towards a descending aorta of the aortic arch from the connection point, and a second portion devised to extend in a second direction, opposite to the first direction, towards an ascending aorta of the aortic arch from the connection point, when the protection unit is positioned in the aortic arch, in the expanded state.

In some examples, the selectively permeable unit is arranged to asymmetrically extend from the connection point in a first direction towards a descending aorta of the aortic arch and in a second direction towards an ascending aorta of the aortic arch, when the protection unit is positioned in the aortic arch, in the expanded state.

The term "collapsible" used in the context of the present application means that a dimension of a device is reducible to a lesser dimension such that it is arrangeable in a tubular delivery unit, such as a catheter. A collapsible unit is expandable when released or pushed out of the delivery unit. Expandable includes self expandable, e.g. by a shape memory effect and/or resilient elasticity. A collapsible unit is the re-collapsible for withdrawal into the delivery unit and out of the patient.

It should be emphasized that the term "including/having" when used in this disclosure is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the invention are capable of will be apparent and elucidated from the following description of examples of the present invention, reference being made to the accompanying drawings, in which

FIG. 2A is a schematic illustration of the distal end portion of the elongated member with the radially expandable units in the collapsed configuration;

FIG. 2B is a schematic illustration of the distal end portion of the elongated member with the radially expandable units in the expanded configuration;

FIGS. 3A, 3B, 3C, 3D are schematic illustrations of examples of the elongated sheath in the flexible, unlocked configuration;

FIG. 3E is a schematic illustration of the cross sectional view of the elongated sheath in the unlocked state;

FIG. 3F is a schematic illustration of one example of the cross sectional view of the elongated sheath in a locked state;

FIG. 3G is a schematic illustration of another example of the cross sectional view of the elongated sheath in the locked state;

DESCRIPTION OF EMBODIMENTS

Figure 1A:
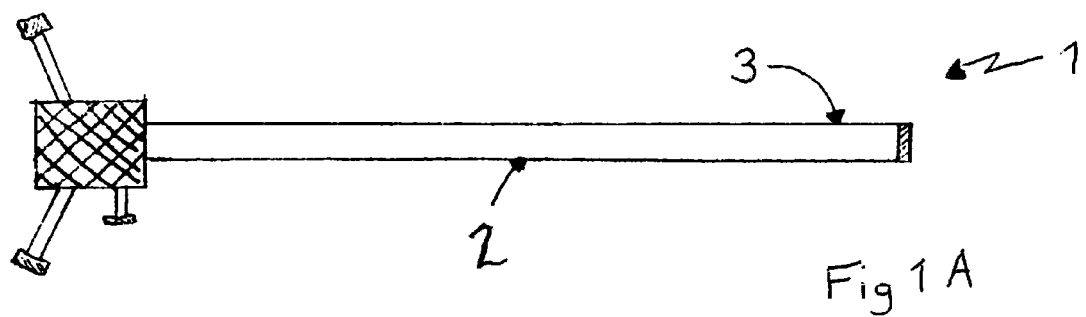
FIG. 1A is a schematic illustration of an elongated sheath connected to a hemostatic valve.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the invention to those skilled in the art. The terminology used in the detailed description of the examples illustrated in the accompanying drawings is not intended to be limiting of the disclosure. In the drawings, like numbers refer to like elements.

Figure 1B:
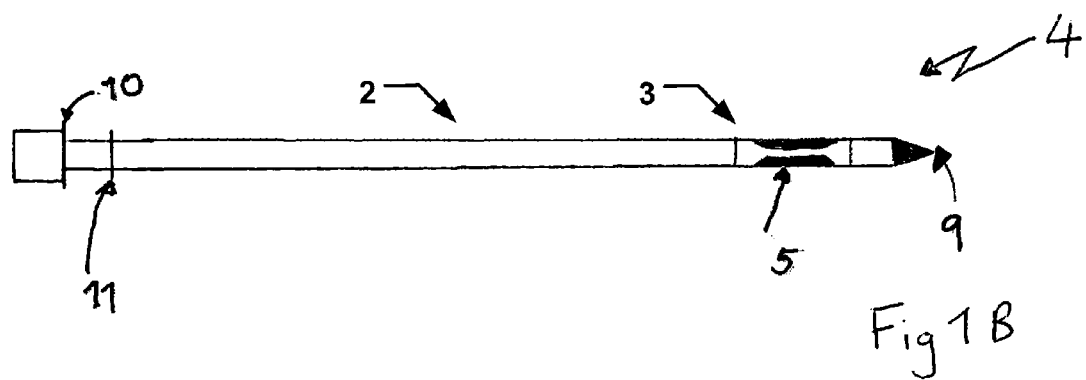
FIG. 1B is a schematic illustration of an elongated member, with the radially expandable units in the collapsed configuration.

In an example of the disclosure according to FIG. 1A, a catheter device 1 for transvascular delivery of a medical device to a cardiac valve region 6 (see e.g. FIG. 4D) of a patient is shown. The catheter device comprises an elongated sheath 2 with a lumen and a distal end 3. In addition, in FIG. 1B an elongated member 4 is provided with a distal end portion 9 comprising a plurality of radially expandable units 5. The end portion 9 may include an obturator. The expandable units 5 are arranged for temporarily positioning the elongated sheath 2 in relation to the cardiac valve 6, FIGS. 4B and 4F. The elongated member 4 is retractably insertable into the lumen of the elongated sheath 2 and the elongated sheath 2 comprises releasable locking members for controllably locking the elongated sheath 2 in a shape at least partly along its length from a relaxed state (See FIG. 3B, and FIG. 4A-B, 4F) to a locked state (See FIG. 3C-D, and FIG. 4D-E, 4G-H) when positioned in relation to the cardiac valve 6 by the expandable units 5.

The elongated sheath 2 depicted in FIG. 1A is designed to be deliverable transvascularly in the relaxed state which facilitates optimal flexibility when transiting through the vasculature. When at the desired anatomical location the elongated sheath 2 is able to transit from the relaxed state to the locked state by activation of the locking members, when positioned in relation to the cardiac valve 6, as seen in FIG. 4D-E, by the expandable units 5, which facilitates optimal stabilization of the catheter 1 for subsequently affixing the medical device to the heart valve 6.

Figure 4A:
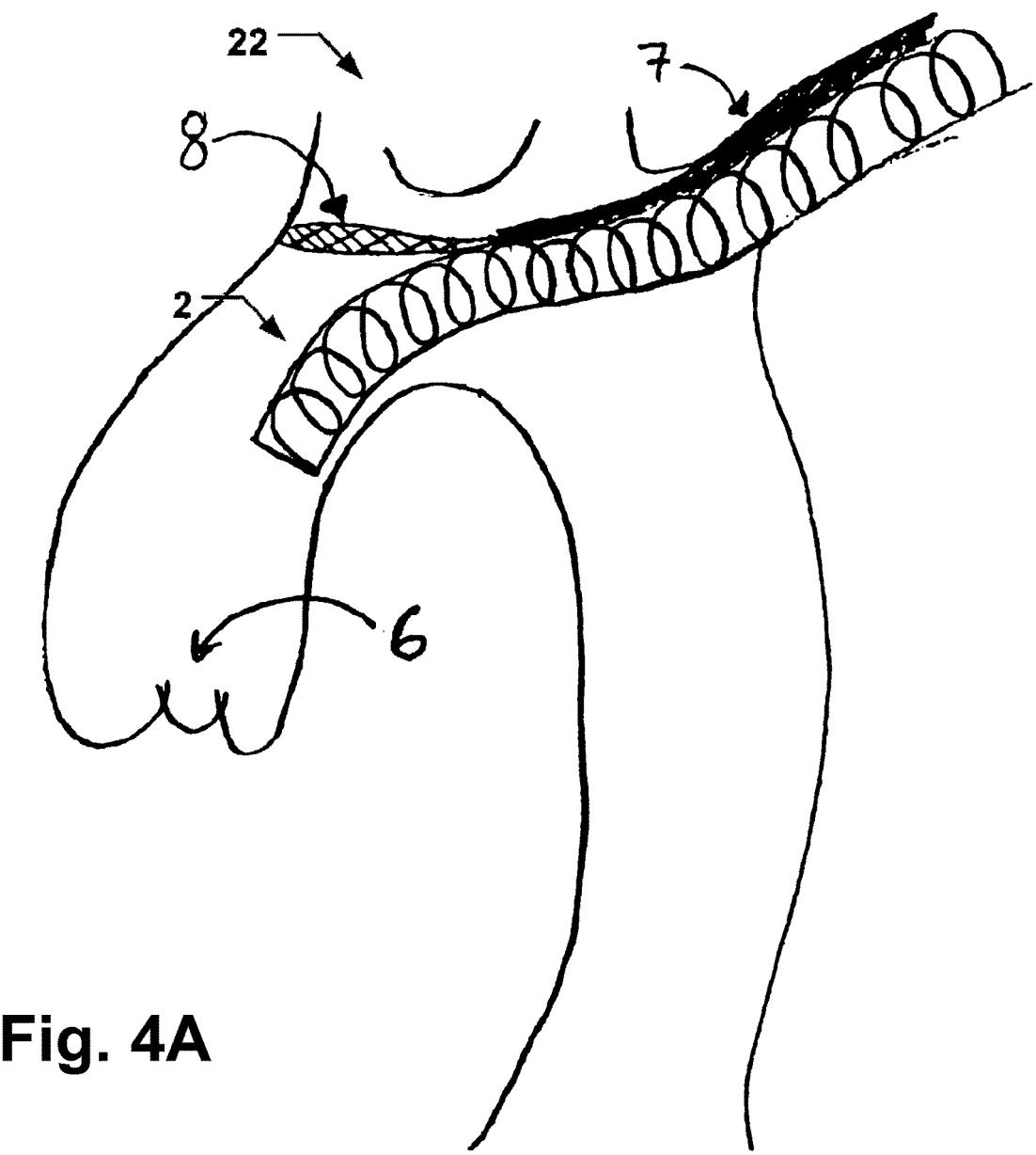
FIG. 4A is a schematic illustration of the elongated sheath delivered transaxillary to a cardiac valve, where an embolic protection filter is deployed, and the sheath is in a relaxed state.
Figure 4B:
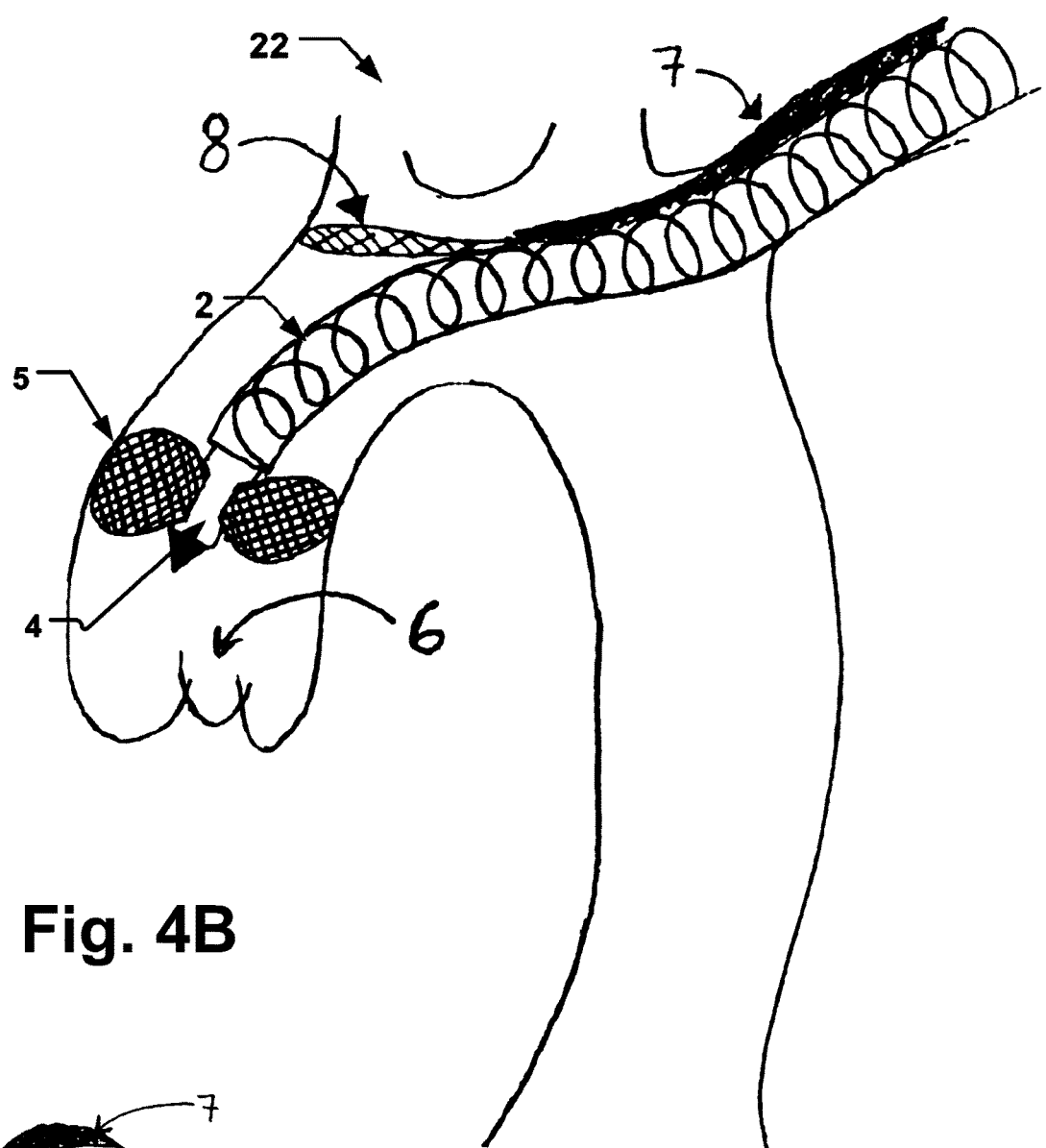
FIG. 4B is a schematic illustration where the relaxed sheath is positioned in relation to the cardiac valve by expandable units of an elongated member extending outside the distal end of the sheath.
Figure 4C:
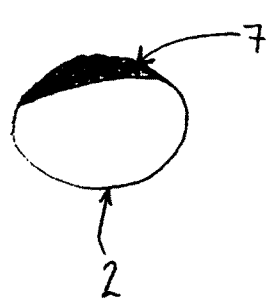
FIG. 4C is a schematic illustration of the cross sectional view of the elongated sheath incorporating a second channel for delivering the embolic protection filter.
Figure 4D:
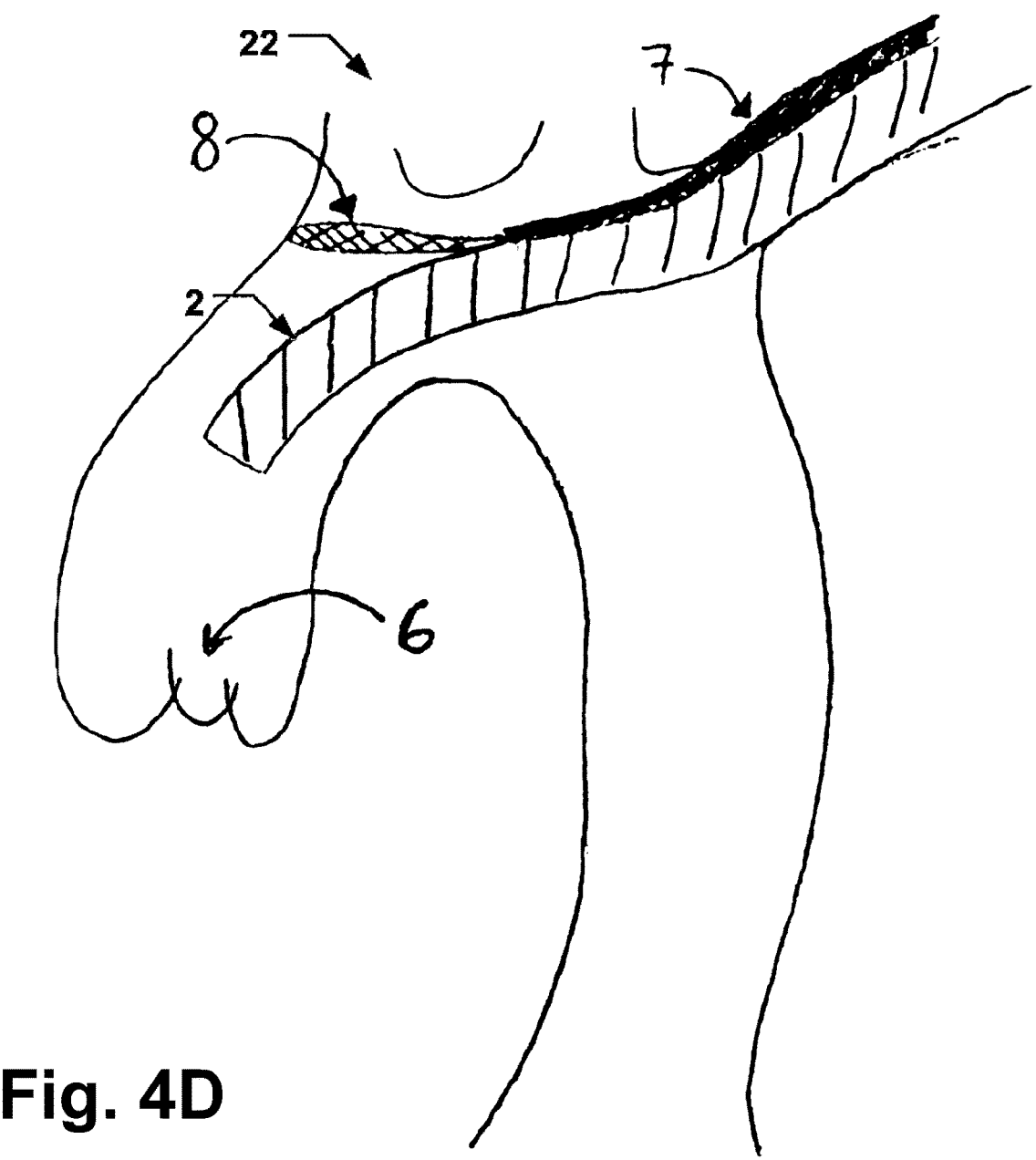
FIG. 4D is a schematic illustration of the elongated sheath delivered transaxillary to a cardiac valve, and the sheath is in the locked configuration arranged relative to an aortic cardiac valve, and the expandable units being withdrawn after positioning the sheath.
Figure 4E:
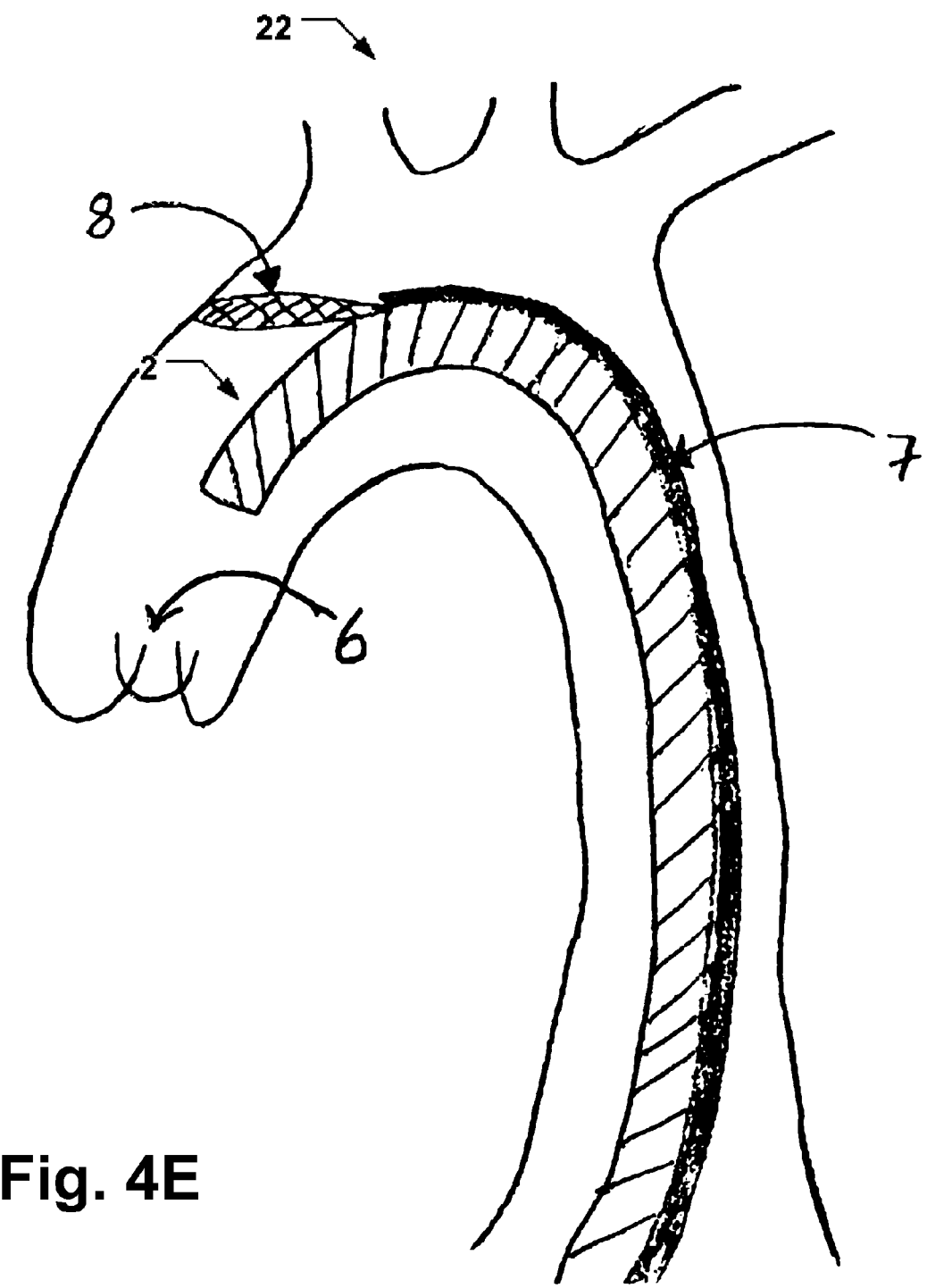
FIG. 4E is a schematic illustration of the elongated sheath delivered transfemorally to a cardiac valve, where an embolic protection filter is deployed and the sheath in the locked configuration.

FIG. 4A shows the elongated sheath inserted in its relaxed shape. FIG. 4B shows the radially expandable units 5 in their expanded configuration, i.e. outside the elongated sheath 2, which positions the elongated sheath 2 centrally over the valve 6. The expandable units 5 expand out of the elongated member 4, which extends beyond the distal end of the sheath 2. Thereafter the elongated sheath 2 is brought to its locked state by locking members, and the elongated member 4 is retractable from the lumen of the elongated sheath 2 together with the plurality of radially expandable units 5 when collapsed, as seen in FIGS. 4D-E. The sheath 2 is now positioned and stabilized over the valve 6. This overcomes the problems in prior art with insufficient stabilization and lack of accurate positioning. Merely providing an expandable catheter could not provide stabilization as with the locking members of the sheath 2. Expandable catheters have another purpose, which is providing an accessible lumen or dilating septum punctures. Further, expandable members of previous catheters are merely for providing aforementioned expansion and not for positioning the catheter centrally over a valve as provided by catheter 1. When the elongated sheath 2 is locked and, when the elongated member 4 is retracted, the lumen of the elongated sheath 2 is accessible for delivery of a medical device to the cardiac valve 6 region.

Figure 4F:
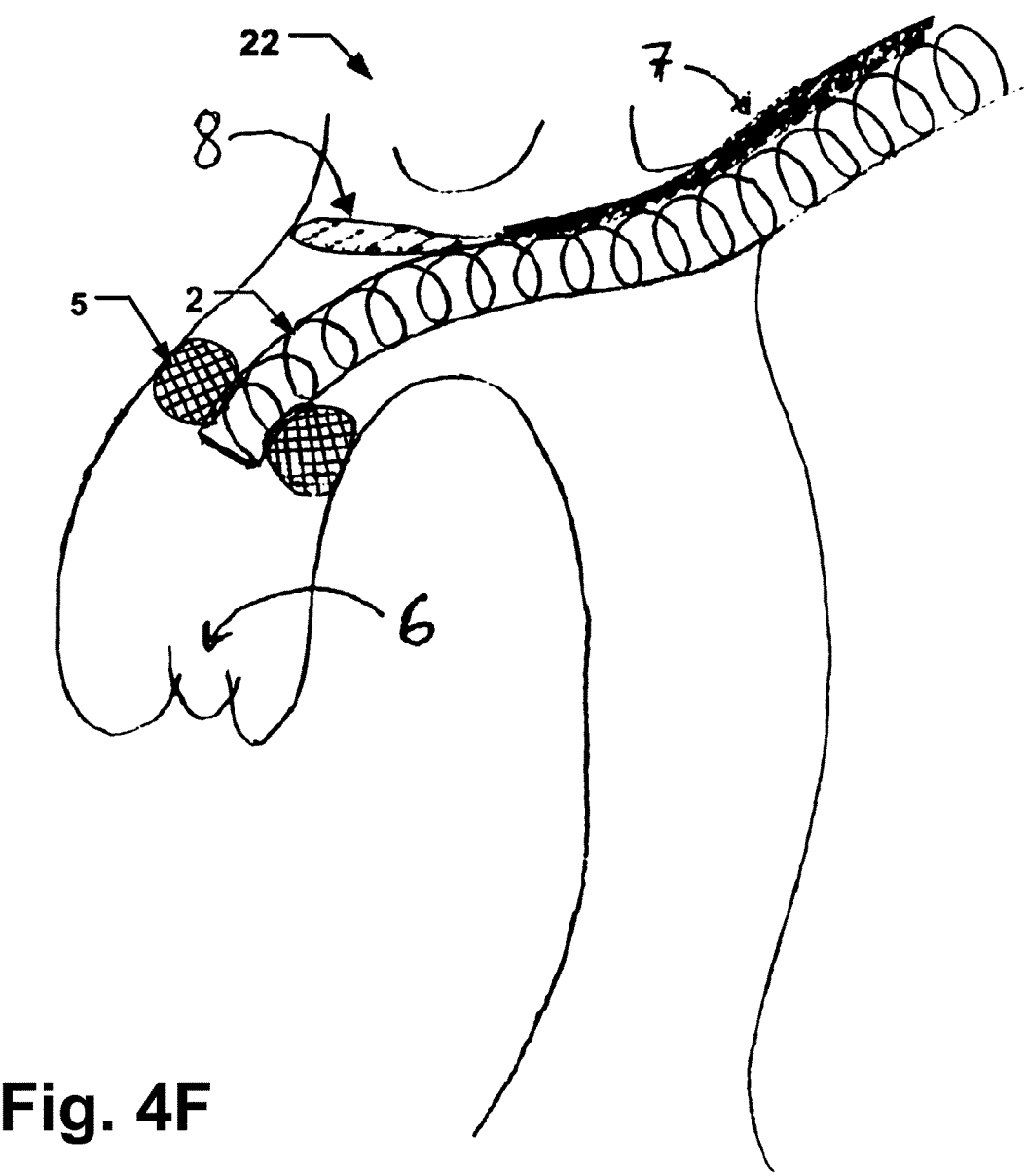
FIG. 4F is a schematic illustration of the elongated sheath delivered transaxillary to a cardiac valve, and where the relaxed sheath is positioned in relation to the cardiac valve by expandable units of the sheath.

Alternatively, or in addition, expandable units, such as balloons may be arranged on the outside of the sheath 2. The expandable unit may be integrally formed with the sheath, as seen in FIG. 4F. Thus, the expandable units do not affect the cross section of the lumen of sheath 2. Upon returning to the unexpanded state, e.g. by deflating balloons of the expandable units 5, a delivery of a medical device through the catheter lumen may be made without the need to retract the expandable units 5.

The expandable units provide for a defined positioning of the distal end of the catheter sheath 2 in an anatomical structure, like a blood vessel, an atrium or cardiac chamber, relative a cardiac valve. This allows for a precision delivery of a medical device through the catheter device. Movements of certain anatomical structures are very limited over the cardiac cycle. For instance the aortic arch is relatively stable and the locked catheter will stay substantially in the same spatial orientation, direction, and distance to the cardiac valve as during the final positioning provided by the expanded expandable units 5.

The catheter may thus be positioned relative a cardiac valve in an anatomical structure.

The catheter may be locked in the locked configuration along its entire length. Alternatively, it may only be locked along a distal portion thereof. A distal portion may for instance be the portion arranged in the ascending aorta, the aortic arch and the descending aorta, as shown in FIG. 4E. The catheter may comprise an embolic protection unit 8, such as an embolic protection filter 8. The embolic protection unit 8, when protruding out of the second lumen 7 and being in apposition against the surrounding vessel wall, may further contribute to stabilizing the distal end of the locked catheter in place relative to the cardiac valve. Hence, when the embolic protection unit 8 is expanded it will function as an anchor to the sheath because it prevents movement of the sheath 2 in the aortic arch due to the second channel 7, from which the embolic protection unit expands, is fixed to the sheath. The delivery unit 13 for the embolic protection unit 8 has sufficient rigidity to allow an anchoring function for the sheath 2. The embolic protection unit 8 provides stabilization and anchoring of the sheath 2 irrespectively whether the sheath 2 is in a relaxed state or in a locked state. Further, the embolic protection unit 8 provides stabilization and anchoring of the sheath 2 irrespectively whether expandable units 5 are used. Hence, it is not essential for the sheath 2 to have the locking members, the elongated member 4, or the expandable units 5, in order to provide the advantageous effects as described, see further below.

FIG. 4D is a schematic illustration of the elongated sheath delivered transaxillary to a cardiac valve, here the aortic valve 6. The embolic protection filter 8 is deployed, and the sheath 2 is in the locked configuration arranged relative to an aortic cardiac valve 6.

FIG. 4E is a schematic illustration of the elongated sheath delivered transfemorally to a cardiac valve, where an embolic protection filter is deployed and the sheath in the locked configuration.

In FIGS. 4D and 4E, the expandable units 5 are not shown, as they are either retracted from the sheath, or returned to their low profile unexpanded/collapsed configuration in the sheath.

Figure 4G:
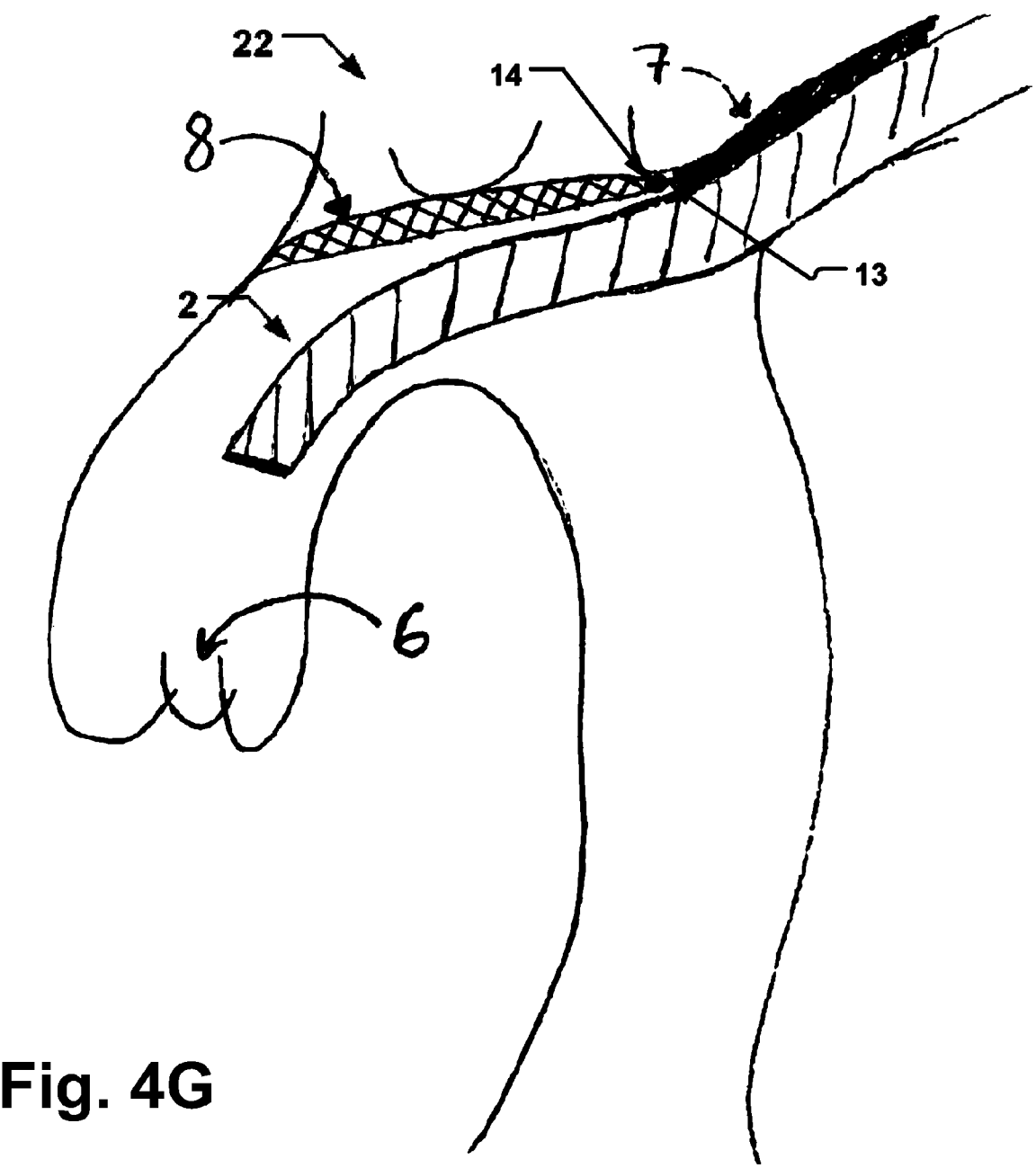
FIG. 4G is a schematic illustration of the elongated sheath delivered transaxillary to a cardiac valve, and where an embolic protection filter is deployed over the vessels in the aortic arch via a second channel of the sheath.
Figure 4H:
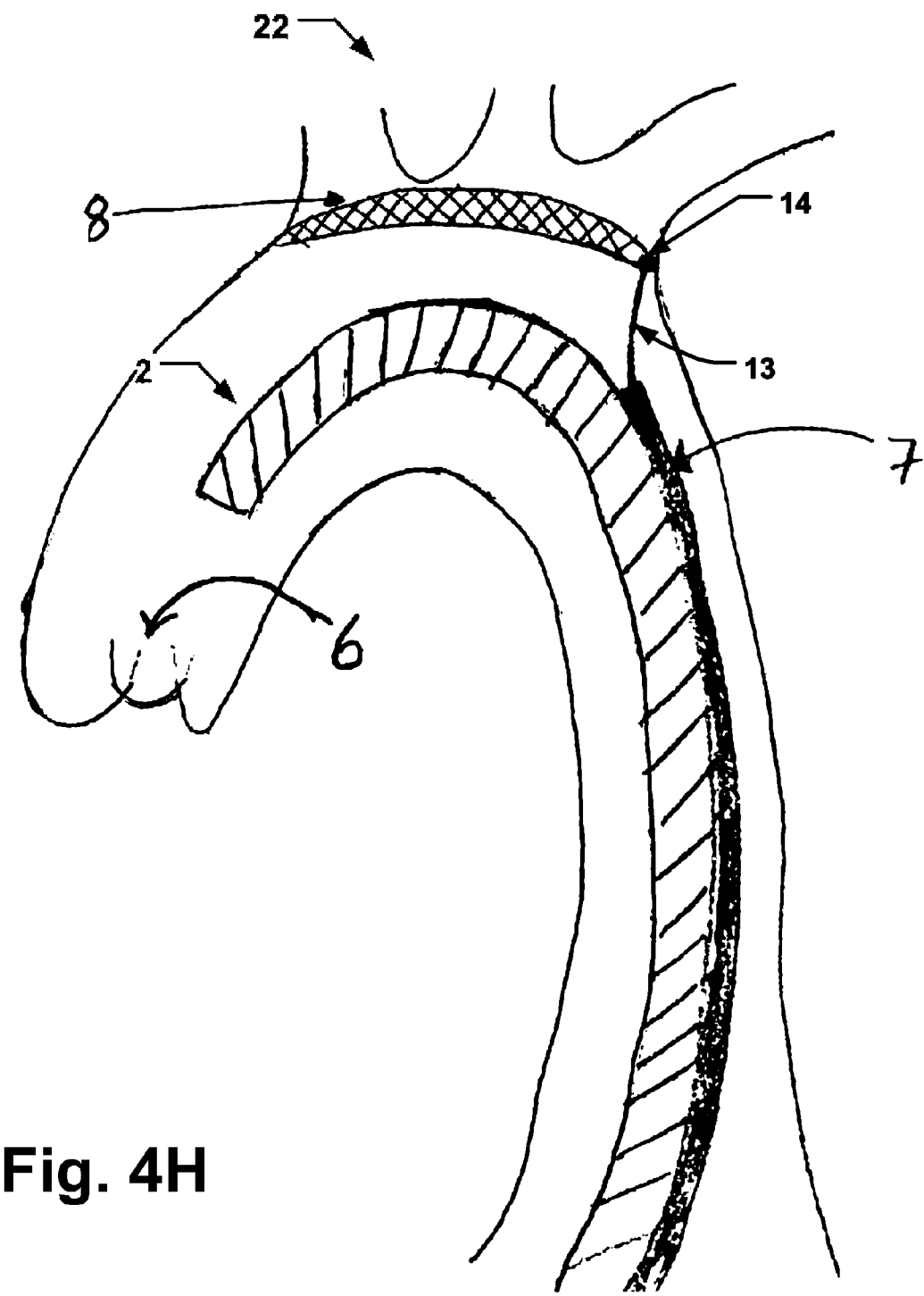
FIG. 4H is a schematic illustration of the elongated sheath delivered transfemorally to a cardiac valve, and where an embolic protection filter is deployed over the vessels in the aortic arch via a second channel of the sheath.

In FIG. 4G-H the embolic protection filter 8 is positioned over two or three of the vessels in the aortic arch, respectively.

In all configurations shown in FIGS. 4A-B, 4D-H, the side vessels 22 are effectively protected from embolic particles entering from the aortic arch. Embolic particles are carried with the blood flow past the embolic protection device along the aortic arch to anatomical structures that are less sensitive than e.g. the brain to which some of the side vessels 22 lead the blood flow. Embolic protection units may be filter units in which the embolic particles are caught. Alternatively, or in addition, the embolic protection units may provide for the particles to slide along the protection unit, but not pass it or fasten in it.

In examples, such as illustrated in FIG. 4A-H a catheter 1 having a second channel 7 that extends parallel on the outer portion or the inner portion of the elongated sheath 2 is depicted. This channel 7 allows for the delivery of further units for example an embolic protection device 8 or liquids to aid the procedure to place the medical device, when the lumen of the elongated sheath 2 is used for the elongated member 4 or medical device.

The second channel 7 may be an integral part on the inside or outside of the elongated sheath 2. This has the advantage of being relatively cheap to manufacture by an extrusion method.

In FIGS. 4A-H, an expandable embolic filter 8 example is depicted. The embolic protection or filter device 8 may be extended before extending the aforementioned expandable units 5. This potentially enhances patient safety by capturing any emboli such as plaque debris produced from the treatment of a stenotic valve, and thus reduces the chance for serious complications such as stroke. In these figures at least a portion of the expandable embolic filter 8 extends from the orifice of the side channel 7 through which the embolic filter 8 is passed. The embolic filter may be of the type as disclosed in WO 2010/026240, which is incorporated herein in its entirety for all purposes. The embolic filter unit may be non-tubular, extending substantially planar in the expanded state. This provides for a compact device and efficient blocking of side branch vessels in the aortic arch from embolies. Interaction with the side walls in the aortic arch is therefore also kept at the minimum, avoiding scraping off further debris to be transported with the blood stream. Simultaneously, the aortic arch is kept open for unrestricted navigation of the sheath 2. Hoop shaped baskets in previous devices scrapes against the vessel wall and blocks a substantial portion of the navigational space in the aortic arch.

Extending "planar" in this context means that the thickness of the device is substantially smaller than the longitudinal extension thereof. Moreover, "planar" means such dimensions perpendicular to the longitudinal extension of the protective material, that blood flow through the aortic arch is not hindered by the protective device.

By having a second channel in the sheath 2, the distal end of the sheath can be positioned appropriately at the valve, by the stabilizing and anchoring effect of the protection unit 8 extending from the second channel, while medical device can be delivered through the lumen of the sheath without any hindrance from the protection unit 8 or e.g. expandable units such as balloons, while at the same time the side branch vessels of the aortic arch are protected from embolies that may be transported in the blood stream from the procedure performed at the valve.

The catheter device 1 may comprise a delivery unit 13 connectable to the embolic filter unit 8 at a connection point 14, as illustrated in FIGS. 4G-H. The connection point 14 is arranged off-centre at the embolic filter unit such that the delivery unit 13 is connectable off-center to the embolic filter unit 8. The off-centre position of the embolic filter unit is advantageous for deploying it with the sheath 2 via the delivery unit 13, while efficiently protecting the carotid arteries from embolies, when carrying out the intervention. Blood flow is kept open efficiently by such compact device. The term "off-centre" used in the context of the present application means eccentric, or not arranged or located in a center of the device. The center is e.g. a center of a circular unit, a focal point of an elliptical unit, a point on a center line, such as a longitudinal center line of an elongated unit, etc. A periphery of a unit is located "off-centre" as it is arranged at a distance in relation to a center of the unit.

Figure 2C:
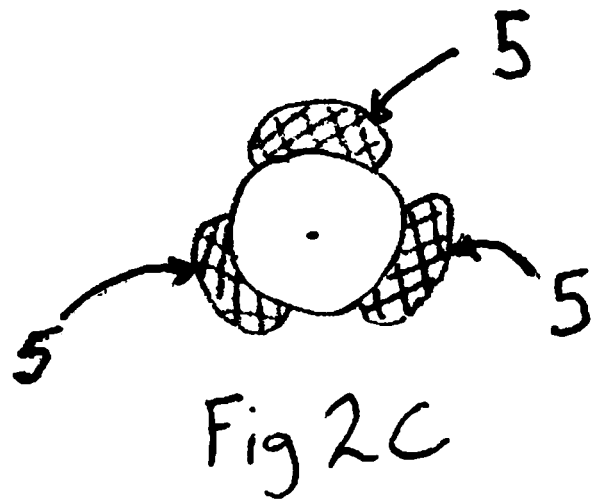
FIG. 2C is a schematic illustration frontal view of the distal end portion of the elongated member with the radially expandable units in the collapsed configuration.
Figure 2D:
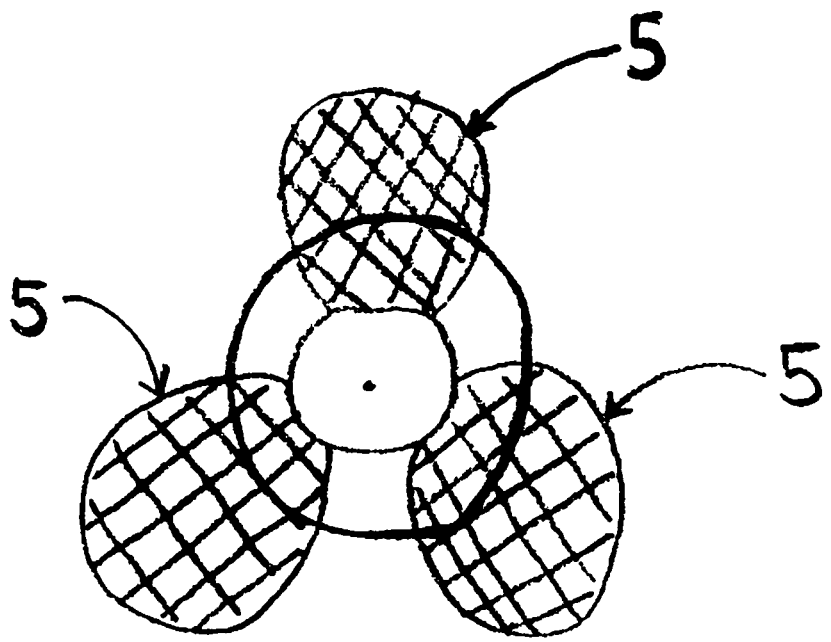
FIG. 2D is a schematic illustration frontal view of the distal end portion of the elongated member with the radially expandable units in the expanded configuration.

The elongated member 4 may be comprised of three balloons positioned radially equidistant around the longitudinal axis (See FIGS. 2C and D). Fewer or more balloons are possible, as well as alternative expansion units such as expandable mechanical levers, or swellable units for example retractable sponges. The expansion units 5 allow for optimal positioning of the elongated sheath 2 in relation to the aforementioned cardiac valve 6. The multiple balloon expansion unit can be expanded (See FIG. 2D) using a variety of means for example using a fluid means or where appropriate gaseous means. The balloons can also be individually or simultaneously expanded as well as inflated to differing pressures independently of the other expanding units.

Alternatively, the elongated member 4 is retractably inserted into the lumen of the elongated sheath 2 to a length equal to the distance between the distal end 9 and the second proximal marker 10. In this example, proximal markers 10 and 11 are used to guide the positional orientation of the distal end portion 9 and thus provide for optimal alignment of the expandable units 5 with the portion of the elongated sheath 2 to be expanded. This facilitates safe positioning at the desired valve region.

In a further example, the elongated sheath 2 is comprised of radiopaque material, facilitating visualization of the elongated sheath 2 which provides for optimal positioning of the elongated sheath 2 for delivery of the medical device. Alternatively, radiopaque fiducial markers on the elongated sheath 2 can be used for optimal positioning of the sheath 2 within the body of the patient.

The example shown in FIGS. 2A and 2B, includes a guide wire 12 which is firstly positioned within the patient which facilitates optimal transit of the elongated sheath 2 and elongated member 4 to the desired anatomical site.

In the examples of FIGS. 3-4, the locking units may comprise releasable latches although any one from draw strings, squeezing mechanisms, or the like could be envisaged as being used to lock the elongated sheath 2 in a locked state, i.e. a rigid or semi-rigid state of the sheath that allows the sheath 2 to maintain a specific curvature, i.e. reduction in flexibility, and thereby secure its position relative to the anatomy, as seen in e.g. FIG. 4D-E. Further, thermal, electrical, magnetic or chemical properties of the material of the locking units or the elongated sheath 2 itself, may provide variable flexibility for changing between a locked state and a relaxed state.

In a specific example, the elongated sheath may be expanded when in locked configuration. Releasing of locking units when the elongated sheath 2 is in an expanded state locks the elongated sheath 2 in the expanded state and thus retains the optimal position for medical device positioning through the procedure.

The locked elongated sheath 2 may be used in medical procedures to delivery of a medical device to the cardiac valve 6, which could include artificial heart valve prosthesis, an annuloplasty device or leaflet clips.

Figure 5:
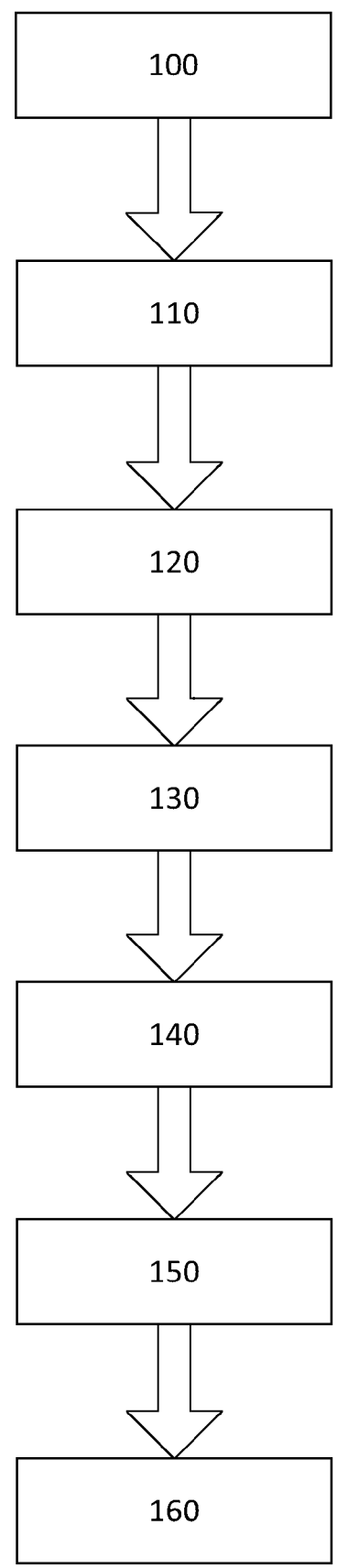
FIG. 5 is a flowchart for a method of implanting a medical device.

The elongated sheath 2 maybe a constituent of a medical system devised for transvascularly delivering a medical device to a cardiac valve 6 of a patient. The method as depicted in FIG. 5 initially comprises 100 minimally invasively either transfemorally (See FIG. 4E) or transaxillary (See FIG. 4D) introducing a catheter 1 comprising an elongated sheath 2 with a lumen in a relaxed state into the patients vascular system. Step 110 involves the distal end 3 of the elongated sheath 2 being navigated through the vascular system to the desired cardiac valve, FIG. 4A. The next step in the system 120, involves the elongated member 4 with a distal end portion 9 comprising a plurality of radially expandable units 5, being inserted into the lumen of the elongated sheath 2, whereupon it is advanced through the elongated sheath 2 to the distal end of the elongated sheath 2, FIG. 4B. Alternatively, expandable units 5 of the sheath may be expanded at this stage (without introducing an elongated member 4 into the sheath, FIG. 4F. Whereupon step 130 is initiated which involves the plurality of radially expandable units 5, being radially expanded to temporarily position in relation to the cardiac valve 6 the elongated sheath 2, (See FIGS. 4B and 4F).

Following positioning, the locking members of the catheter are released to maintain the elongated sheath 2 in a locked state (step 140). Step 150 of the system can then be performed whereby the expandable units 5 are then retracted and the elongated member 4 is withdrawn from the lumen of the elongated sheath 2, FIG. 4D-E. Alternatively, the expandable units 5 of a sheath 2 are brought back to the non-expanded state.

The embolic protection unit as shown in FIGS. 4A-H, may then be advanced out of the second channel 7. In this manner, side vessels are protected from embolic material, such as debris.

A medical device can now be delivered through the lumen of the locked elongated sheath 2 to the heart valve 6. This delivery is done with high spatial precision. Blood flow in the lumen around the locked elongated sheath 2 is affected less than with expanded expandable units 5.

The medical device may for instance be a cardiac valve repair or replacement device.

When the medical device is delivered, release of the locking members to return the elongated sheath 2 to the relaxed state can now be performed (step 160) with the subsequent withdrawal of the elongated sheath 2 in the relaxed state from the vasculature of the patient.

The embolic protection unit as shown in FIGS. 4A-H may be retracted prior or after the release of the locking members.

Locking of the elongated sheath 2 in the locked state (FIG. 3B-D) comprises releasing the locking members for controllably locking the elongated sheath 2 when positioned in relation to the cardiac valve 6 by the expandable units 5. This serves to retain the optimal position for delivery of the medical device during the procedure.

To ensure the optimal positioning of the elongated member 4 when it is inserted into the elongated sheath 2, the elongated member 4 is inserted to a length which is equal to the distance between the distal end and the second proximal marker 10 of the elongated member 4. Primarily the elongated sheath 2 will be centrally positioned in relation to the cardiac valve 6, which facilitates optimal delivery of the medical device, although other positions off-center could also be desirable.

The medical system is primarily used for the delivery of a medical device to be affixed to the particular cardiac valve 6, which include the aortic and mitral valves of a patient. After delivery of the medical device to the cardiac valve 6, the medical device delivery system is withdrawn through the lumen of the locked elongated sheath 2, which may be aided if the elongated sheath 2 is in an expanded state. After removal of the medical device delivery system, the elongated sheath 2 in the locked state transits to the relaxed state which facilitates enhanced retraction of the elongated sheath 2.

Figure 6:
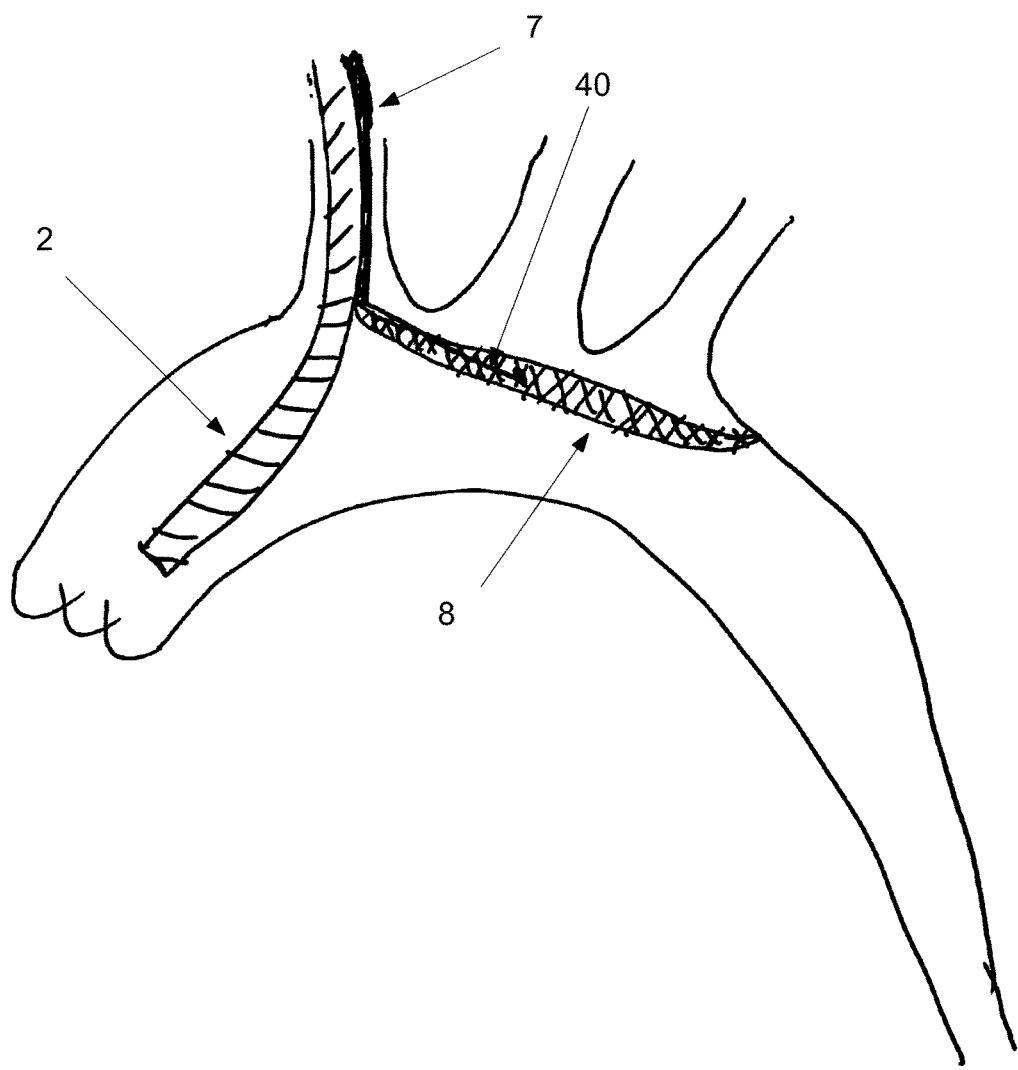
FIG. 6 is a schematic illustration of the elongated sheath delivered transaxillary to a cardiac valve, and where an embolic protection filter is deployed over the vessels in the aortic arch via a second channel of the sheath.

FIG. 6 illustrates an example of using a catheter having two channels, as described herein above, for delivering a embolic protection unit from the brachiocephalic artery, such as from the right subclavia artery or the right common carotid artery. The elongated sheath 2 is advanced into the ascending aorta and may be used to deliver a medical device for a medical procedure. Medical procedures on the heart may includes at least a step related to removal of a heart valve, the placement of a prosthetic heart valve, or repair of a heart valve. This may include the treatment of cardiac valvular disease, like valvuloplasties including percutaneous valve replacement. The procedure may be Transcatheter Aortic Heart Valve (TAVI) involving implantation of a collapsible aortic heart valve with minimally-invasive techniques. It may also relate to bypass, cardiac surgery, interventional cardiology or electrophysiology procedures.

An apposition sustaining unit may be used to apply a force offset to the connection point at the device. Offset to the connection point may for instance be at the periphery. It may also be adjacent the periphery. It may also be centrally of the blood permeable unit within the periphery. The force is applied or directed towards an inner wall of the aortic arch when the device is positioned in the aortic arch. In this manner tissue apposition of the periphery to an inner wall of the aortic arch is supported by the force. For instance, a tractive force such applied may pull a periphery of the device against the inner wall. The force supports locking the device in place upon implantation.

The embolic protection device can thus be reliably placed across the apex of the aorta in order to prevent emboli from flowing into the carotid arteries. The inventive solution is not iatrogenic, as it prevents creation of debris from e.g. ostia of side vessels. Iatrogenic relates to an adverse condition in a patient resulting from treatment by a physician or surgeon. Arms, anchors, delivery shafts, bows, etc. of inferior embolic protection devices, for instance extending into the side vessels, risking scraping off of plaque from the inner vessel wall or ostia, are not needed and can be avoided thanks to the present disclosure.

In the example of FIG. 6 a tether 40 which may run in the same channel or in other channels of the catheter as the embolic protection unit 8 and be used to apply a tractive force. The apposition supporting unit may then be an active traction unit that has for instance at least one operable tether distally connected at the location offset the connection point.

The distal connection location of the tether may be located at the frame, periphery and/or blood permeable unit, of the embolic protection device for providing the tractive force. The tether has one or more distal end(s). The distal end is for instance connected to the periphery of the embolic protection device. The tether's distal end(s) may be connected to the blood permeable unit, such as a filter or deflector membrane. The membrane may be moved by the traction, e.g. if the membrane is flexible and/or elastic.

Tether(s), or more precisely, tetherline(s) are provided to control a sealing degree of the periphery. Tether(s) are provided for direction of apposition towards aortic tissue/ cerebral arteries. The tether may provide active traction by a pull action on the tether communicated to the embolic protection device to which it is distally connected.

The tether 40 may be arranged longitudinally movable relative the delivery unit. In this manner, the device is positionable in the aortic arch so that the delivery device may be locked in a "delivered" position, by the delivery unit, e.g. at its proximal end at or outside a port of an introducer. The tether 40 may then still be movable and improve sealing as described herein.

Tether(s) may be multifilament(s), which provides for a particularly flexible solution advantageous for narrow lumen navigation.

A tether 40 may extend straight across the blood permeable unit to the forward end of the device. Thus the middle line may be pulled up and the periphery is tensioned against the inner wall. The tether provides for a lifting force to the forward end. In case the tether is guided at the middle line, e.g. threaded through eyelets, it may provide a progressive lifting force distributed along the device.

The at least one tether 40 may be longitudinally elastic, i.e. it is longitudinally stretchable and resiliently return to a non-stretched longitudinal extension. The tether may be elastic along its entire length. The tether may include one or more elastic portions or elastic elements. The elastic portion may be a helical wound portion of the tether acting as a spring. The elastic portion may be a tubular braid of a double helically wound strands. The elastic portion may be made of an elastic material, preferably biocompatible, like rubber. In this manner the tractive force is variable. This may be advantageous for preventing rupture of the tether line as a non-linear extension may be "felt" by an operator. This variable traction force may also be advantageous if the tether is tension, applying a desired traction for improving sealing of the embolic protection device. The tether may be locked at its proximal end in this position, e.g. extending out of an introducer port. The elasticity may provide for compensating physiological movements of the aortic arch relative a proximal end of the device and/or tether while maintaining the tissue apposition. The applied force is provided within a certain range suitable to maintain the improved peripheral sealing while the aortic arch moves due to the beating heart and blood pulse waves.

The blood permeable unit of the embolic protection device may have at least one guiding unit, such as an eyelet, a tubular bent element, a roller, an open pocket fabric portion, etc. The guiding unit may receive the tether proximally its distal end where it is attached to the device, such as at the blood permeable unit, flange, or periphery. The guiding units, such as eyelet(s) etc. provide for locally controllable apposition at the device. The traction force may be distributed to different areas of the device.

The device may have an attachment point where a distal end of the tether is connected to the device and a tractive force is transmissible via the attachment point to the device towards the periphery. Optionally one or more radiopaque fiducial markers may be provided at the device. A fiducial marker may be provided at the attachment point. Fiducial markers provide for advantageous X-ray visibility and navigation, position feedback and control of the device.

In some examples, the tether is proximally extending through an ostium into a selected side vessel such that the tractive force centers the device in relation to the ostium. When pulling the tetherline 40, it pulls the device at its periphery against the inner wall of the aorta for locking the device in place. In this manner the device is self aligning in relation to the ostium of the selected side vessel thanks to the tether. The skilled person may provide suitable guiding units for the tether when reading this disclosure to obtain this function.

The device may include multiple tethers distally attached along the periphery. Alternatively, or in addition, a single proximal tetherline may separate distally into a plurality of (sub)tetherlines. For instance, a tether may be branched in the form of a Y. A single tether to be operated proximally may then distribute a tractive force distally via its two distal end points to the embolic protection device.

Multiple tethers may be used or combined with tethers having multiple distal ends. The multiple tethers may be collected proximally at the device, e.g. at a base thereof. In this manner, the device provides for a progressive force that is evenly distributed along the periphery of the device. The device may in this manner advantageously adapt to the inner shape of the aortic arch. The adaptation may even more enhanced by providing longitudinally elastic portions at the tether(s). For instance, the branched (sub)tetherlines may be provided of elastic material, while the main line is substantially non-elastic, but flexible.

In some examples, the device may have at least one rib extending between different, preferably opposite, joints at the periphery, wherein the tether is distally attached at the rib. The tether 40 may thus apply a tractive force to the rib, which in turn transfers the force to the periphery of the device 8 towards the aortic inner wall tissue. The rib may be a beam or yoke. It may be arranged longitudinal or transversal in relation to the expanded device's 8 longitudinal axis.

Figure 7A:
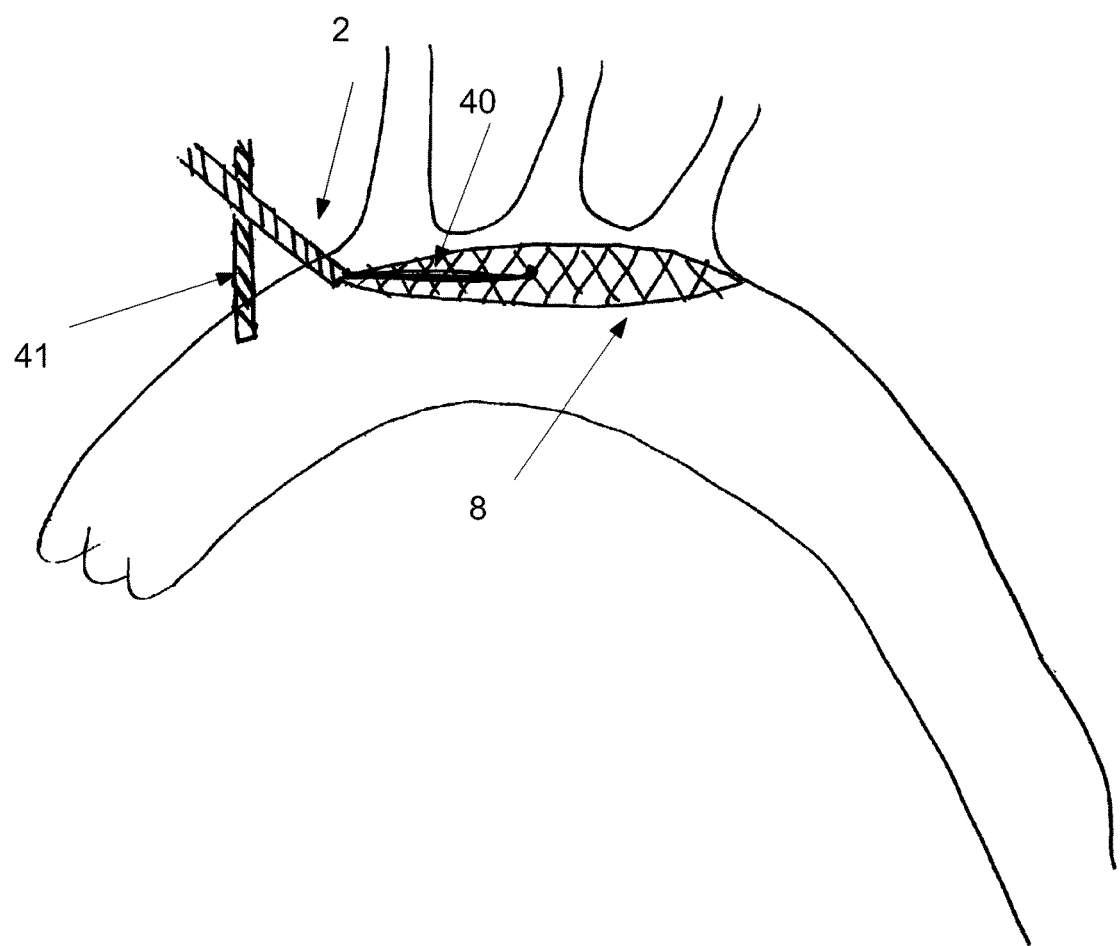
FIG. 7A is a schematic illustration of the elongated sheath delivering an embolic protection filter through a direct aorta access.

FIG. 7A illustrates a "direct aorta" approach were an incision is made through the wall of the ascending aorta. This is done by making a mini-sternotomy or mini-thoracotomy. In the mini-thoracotomy a incision is made in the intercostal space. For TAVI, the direct aorta approach can be used in patients with any aortic root angle. Direct aortic access may be indicated for patients with vessel diameters <6 mm, heavy peripheral calcification, excessive tortuosity or subclavian stenosis. The most appropriate access route should be selected by the cardiovascular team based on patient anatomical and clinical characteristics.

In FIG. 7A, the embolic protection unit 8 is introduced into the aortic arch with one catheter 2 through an incision in the wall. A second incision is positioned upstream the incision used for introducing a medical device or performing a medical procedure. Additionally, the embolic protection unit may have an apposition sustaining unit, such as a tether 8.

Alternatively the brachiocephalic artery may be used for introducing a sheath 2 or catheter for advancing the embolic protection unit into the aorta arch while a incision is used for introducing a medical device or performing a medical procedure.

Figure 7B:
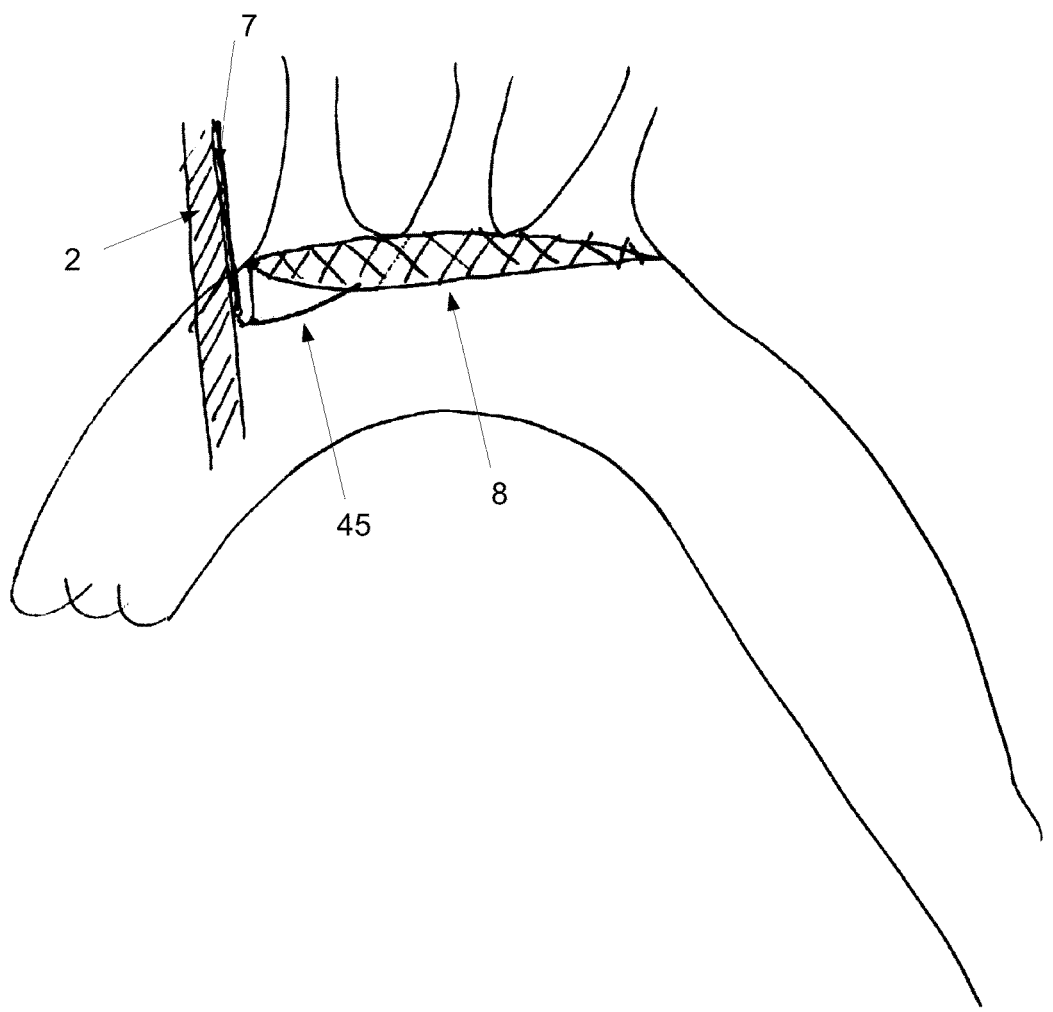
FIG. 7B is a schematic illustration of the elongated sheath delivered through a direct aorta access to a cardiac valve, and where an embolic protection filter is deployed over the vessels in the aortic arch via a second channel of the sheath.

In FIG. 7B illustrates an example of using a catheter having two channels, as described herein above, for delivering an embolic protection unit 8 using the direct aorta approach. The first channel 2 is used for delivering a medical device or performing a medical procedure while the second channel 7 is used for introducing the embolic protection unit 8. In the illustration of FIG. 7B, the apposition sustaining unit is applying a pushing force by a pushing unit 45. A pushing unit is similar to the traction, such as a tether, as described herein above. But instead of a tractive force a pushing force is applied from beneath the embolic protection unit 8. The pushing unit 45 applies pushing force against the frame, periphery and/or blood permeable unit. Thus the pushing force and presses the periphery to the inner wall. This can be done either with a single wire or multiple wires (as shown in the FIG. 7B). The wires may be connected to the embolic protection unit 8 in the same fashion as the tethers described herein.

Figure 8A:
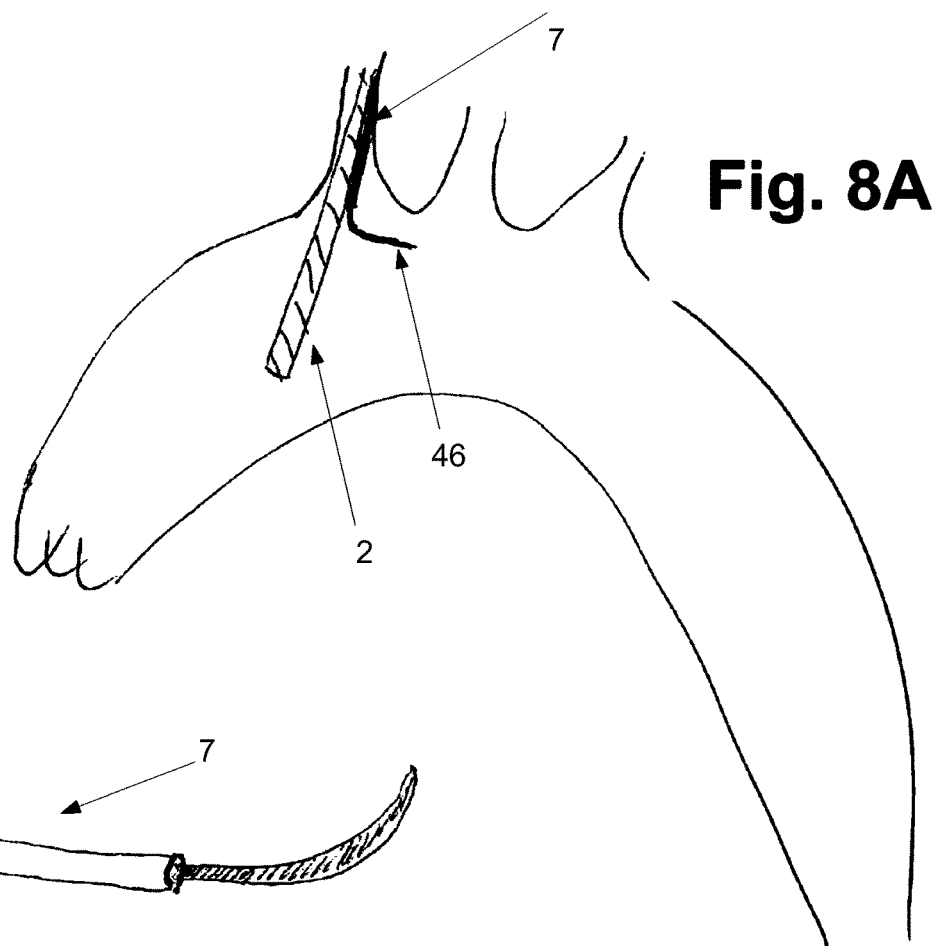
FIG. 8A is a schematic illustration of the elongated sheath delivered transaxillary to a cardiac valve, and where an embolic protection filter is deployed over the vessels in the aortic arch using a retractable sheath via a second channel.
Figure 8B:
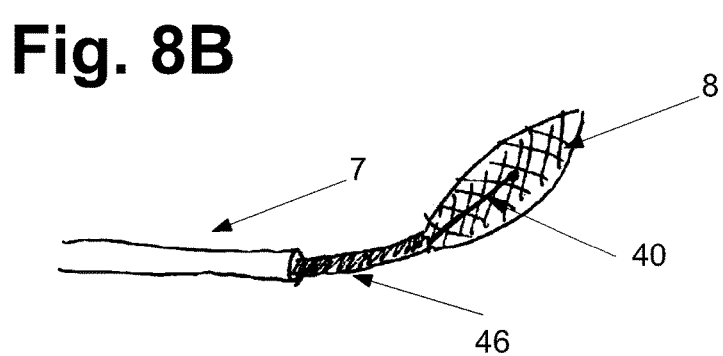
FIG. 8B is a schematic illustration of the retractable sheath advanced from the second channel.
Figure 8C:
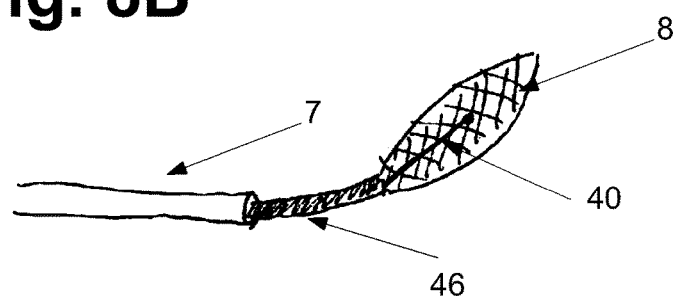
FIG. 8C is a schematic illustration of the retractable sheath when retracting and the embolic protection filter is expanding.

FIG. 8A-C illustrates an example of using a catheter having two channels 2 and 7 introduced from the brachiocephalic artery. In this example, when advancing the embolic protection unit 8, in a downstream direction from the catheter, a second catheter is pushed out of the second channel 7. This second catheter has a retractable sheath 46 enclosing the embolic protection unit 8. When the retractable sheath has reach its correct location the sheath is retracted where after the embolic protection unit expands.

Additionally and/or alternatively to the tether 40 illustrated in FIG. 8C any type of sustaining unit can be used such as a pushing unit.

Additionally, as illustrated in FIG. 8A-C, the retractable sheath has a bent distal end. This may facilitate directing the retractable sheath into the aorta arch.

The same approach using a retractable sheath can be applied on the direct aorta approach or when introducing an embolic protection unit 8 through any of the other accesses, such as the left subclavian artery, or the descending aorta such as in a femoral approach.

Figure 9A:
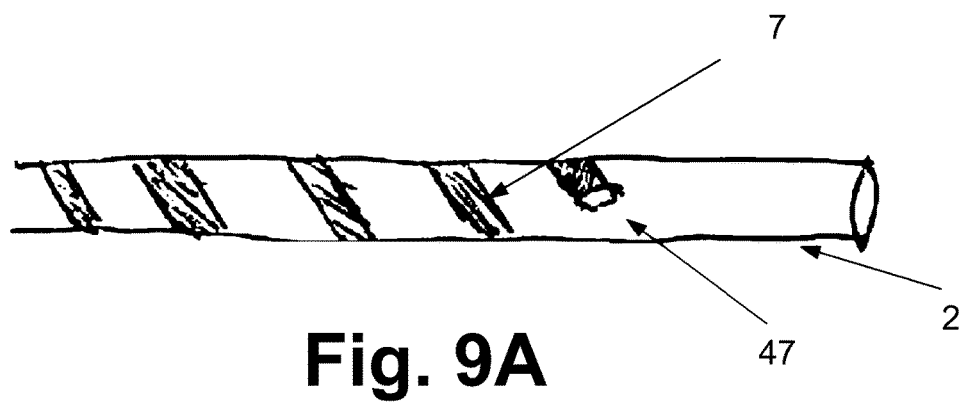
FIG. 9A is a schematically illustration of a sheath with a second channel helically arranged at the sheath.

FIG. 9 A-B, illustrates another example of how the directing of the embolic protection unit 8 into the aorta arch may be facilitated. In this example, the second channel 7 is arranged helically around elongated sheath 2. Thus the opening 47 of the second channel may be directed at an angle away from an opening of the first channel of the elongated sheath 2, towards the aorta arch.

Additionally, this arrangement may be used with a retractable sheath as described in relation with FIG. 8A-C.

Figure 9B:
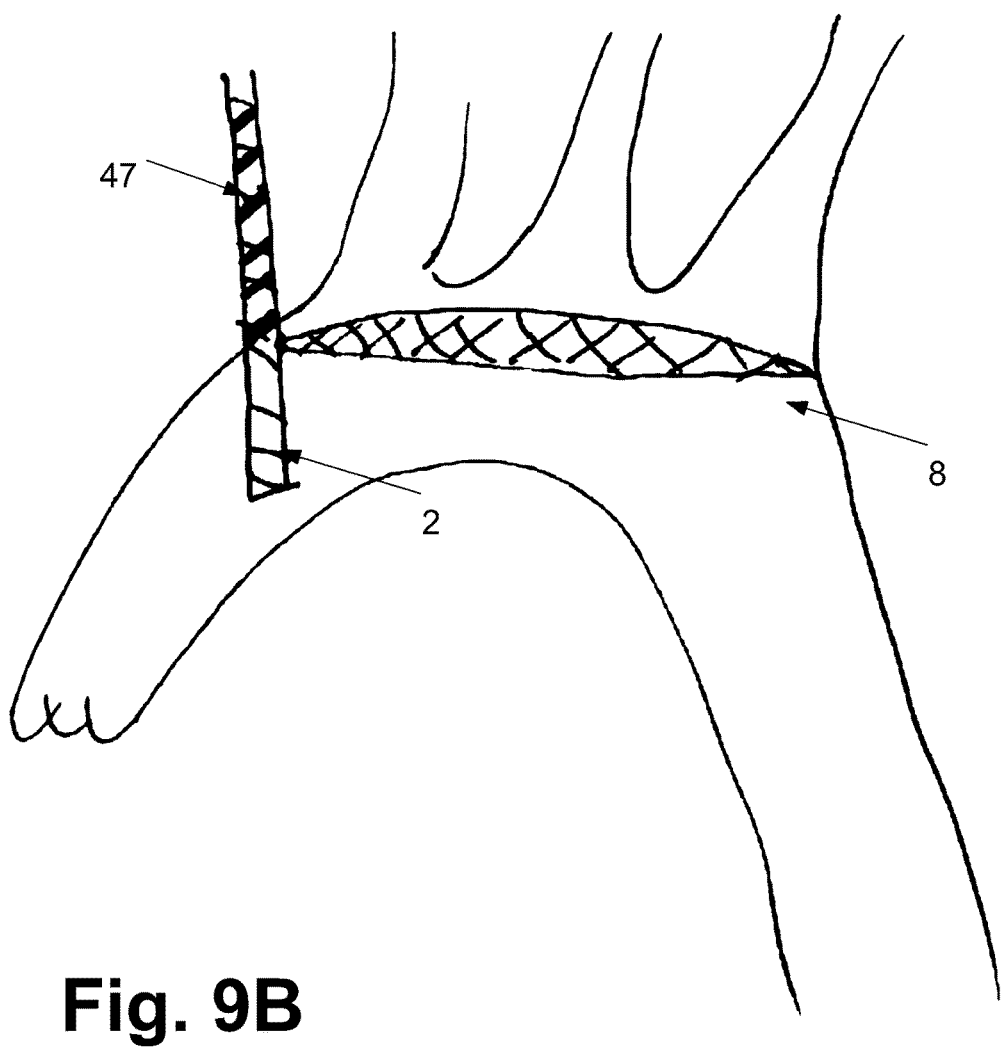
FIG. 9B is a schematic illustration of the elongated sheath delivered through a direct aorta access to a cardiac valve, and where an embolic protection filter is deployed over the vessels in the aortic arch via a second channel helically arranged at the sheath.

FIG. 9B illustrates a direct aorta approach but this may be used when introducing a catheter from the brachiocephalic artery.

Additionally to what has been described above, delivering of the embolic protection device may be made transluminally, and delivering the first catheter may be performed after the delivering the embolic protection device.

Delivering the first catheter may include placing a balloon mounted on the first catheter with expanding the balloon in the ascending aortic arch to lock a distal end of the first catheter in place. The balloon may have a donut shape having a filter between the catheter and the inner ring of the donut shape.

The embolic protection device used in the method may extends from a distal end of a second catheter or separate channel of the first catheter, such that the position of the embolic protection device can be independently adjusted from the position of the first catheter.

Delivering a first catheter may be performed concurrently with delivering the embolic protection device via a separate channel of the first catheter, independent of the endovascular procedure.

The present invention has been described above with reference to specific examples. However, other examples than the above described are equally possible within the scope of the invention. Different method steps than those described above, may be provided within the scope of the invention. The different features and steps of the invention may be combined in other combinations than those described. The catheter may be positioned and locked in other cardiac anatomical structures than illustrated. Medical devices delivered through the catheter sheath may be any medical device to be delivered to the cardiac valve tissue. The scope of the invention is only limited by the appended patent claims.

The invention claimed is:

1. A method of delivering an embolic protection unit to an aorta arch of a patient comprising:
   introducing a catheter through an incision in a wall of an ascending aorta of the patient, said catheter comprising an embolic protection unit having an off-center connection point;
   advancing said embolic protection unit in a downstream direction from said catheter;
   expanding said embolic protection unit in the aorta arch to cover an ostia of the patient;
   delivering a medical device into the ascending aorta while said embolic protection unit is held by said catheter covering said ostia; and
   making an incision in a wall of the ascending aorta upstream of said introduced catheter for introducing said medical device while said embolic protection unit is protecting said ostia.

2. The method according to claim 1, wherein said embolic protection unit is expanded to a non-tubular, substantially planar shape over said ostia.

3. The method according to claim 1, wherein said catheter is introduced towards a cardiac valve coaxially in said ascending aorta, or wherein said medical device is introduced towards said cardiac valve coaxially in said ascending aorta.

4. The method according to claim 1, wherein said catheter comprises an elongated sheath with a first channel and a second channel from which said embolic protection unit is expanded, said second channel is arranged within said first channel or said catheter comprises an elongated sheath with a first channel and a second channel is arranged around said elongated sheath.

5. The method according to claim 4, comprising introducing a pigtail through one of said channels.

6. The method according to claim 4, wherein said second channel is arranged helically around said elongated sheath, and wherein said second channel has an opening directed at an angle away from an opening of said first channel in a direction toward the aorta arch when said opening of said first channel is directed towards the ascending aorta.

7. The method according to claim 4, further comprising,
   radially expanding expandable units of said catheter or an elongated member positioned beyond a distal end of said elongated sheath, to temporarily position in relation to said valve said elongated sheath;
   releasing locking members of said catheter to maintain said elongated sheath in a locked state;
   delivering a medical device through said first channel to said cardiac valve;
   releasing said locking members to return said elongated sheath to a relaxed state; and
   withdrawing said elongated sheath in said relaxed state from the vasculature of said patient.

8. The method according to claim 7 further comprising, inserting an elongated member with a distal end portion comprising a plurality of said radially expandable units into said first channel of said elongated sheath;
advancing said elongated member through said elongated sheath to said distal end of said elongated sheath;
retracting said expandable units and withdrawing said elongated member from said first channel of the elongated sheath.

9. The method according to claim 1, wherein said medical device is a bypass machine.

10. The method according to claim 1, wherein said medical device is for a TAVI procedure where a stent valve is delivered while said embolic protection unit is positioned and with said catheter in said aorta arch.

11. The method according to claim 1, wherein said medical device is a device for electrophysiology.

12. Method The method according to claim 1, wherein advancing said embolic protection unit in a downstream direction from said catheter comprises,
advancing a second catheter through a channel of said catheter, said second catheter has a retractable sheath enclosing said embolic protection unit;
retracting said sheath whereby said embolic protection unit expands.

13. The method according to claim 12, wherein said second catheter has a distal end having a bend.

14. A method of delivering an embolic protection unit to an aorta arch of a patient comprising:
introducing a catheter from a brachiocephalic artery or through an incision in a wall of an ascending aorta of the patient, said catheter comprising an embolic protection unit having an off-center connection point;
advancing said embolic protection unit in a downstream direction from said catheter;
expanding said embolic protection unit in the aorta arch to cover an ostia of the patient;
delivering a medical device into the ascending aorta while said embolic protection unit is held by said catheter covering said ostia; and
introducing said catheter in a direction towards said aorta arch;
retracting said catheter after expanding said embolic protection unit in said aorta arch;
forwarding said catheter towards a cardiac valve coaxially in said ascending aorta; and
using at least one tissue apposition sustaining unit, not being a delivery shaft of said embolic protection unit, for application of a force offset to said connection point at said embolic protection unit towards an inner wall of said aortic arch when said embolic protection unit is positioned in said aortic arch such that tissue apposition of a periphery to an inner wall of said aortic arch is supported by said force.

15. The method according to claim 14, wherein said supported apposition is improving apposition of said periphery to said inner wall of said aortic arch, such that said improved apposition provides for improved sealing of said periphery against said inner wall.

16. The method according to claim 15, wherein said force is applied in a substantially proximal direction relative said device for said improved sealing.

17. The method according to claim 14, wherein applying said force includes applying a tractive force by a traction unit or a pushing force by a pushing unit.

18. A method of delivering an embolic protection unit to an aorta arch of a patient comprising:
introducing a catheter from a brachiocephalic artery or through an incision in a wall of an ascending aorta of the patient, said catheter comprising an embolic protection unit having an off-center connection point;
advancing said embolic protection unit in a downstream direction from said catheter;
expanding said embolic protection unit in the aorta arch to cover an ostia of the patient; and
delivering a medical device into the ascending aorta while said embolic protection unit is held by said catheter covering said ostia;
wherein said introducing said catheter includes placing a balloon mounted on said catheter and expanding said balloon in the ascending aorta; and
wherein said balloon is a donut shaped balloon having a filter between said catheter and an inner ring of said donut shape.

* * * * *